US012702686B2

(12) United States Patent
Gallo et al.

(10) Patent No.: US 12,702,686 B2
(45) Date of Patent: Aug. 11, 2026

(54) ANTIMICROBIAL THERAPY

(71) Applicant: The Regents of the University of California, Oakland, CA (US)

(72) Inventors: Richard L. Gallo, San Diego, CA (US); Teruaki Nakatsuji, San Diego, CA (US); Kate Worthing, Tucson, AZ (US); Alan O. O'Neill, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 405 days.

(21) Appl. No.: 18/265,653

(22) PCT Filed: Jan. 26, 2022

(86) PCT No.: PCT/US2022/013921
§ 371 (c)(1),
(2) Date: Jun. 6, 2023

(87) PCT Pub. No.: WO2022/164916
PCT Pub. Date: Aug. 4, 2022

(65) Prior Publication Data
US 2024/0058395 A1 Feb. 22, 2024

Related U.S. Application Data

(60) Provisional application No. 63/141,876, filed on Jan. 26, 2021.

(51) Int. Cl.

| | |
|---|---|
| ***A61K 39/02*** | (2006.01) |
| ***A61K 9/00*** | (2006.01) |
| ***A61K 35/741*** | (2015.01) |
| ***A61P 31/04*** | (2006.01) |

(52) U.S. Cl.
CPC .......... *A61K 35/741* (2013.01); *A61K 9/0014* (2013.01); *A61P 31/04* (2018.01)

(58) Field of Classification Search
None
See application file for complete search history.

(56) References Cited

U.S. PATENT DOCUMENTS

2020/0246397 A1 8/2020 Nakatsuji et al.

OTHER PUBLICATIONS

Worthing et al (Vet. Microbio. 2018. 222: 98-104; Uniprot. Accession No. A0A2K3Z291).*
Tang, Xiaofan, International Preliminary Report on Patentability and Written Opinion, PCT/US2022/013921, The International Bureau of WIPO, Aug. 10, 2023.
Bierowiec et al., "Prevalence of *Staphylococcus* Species Colonization in Healthy and Sick Cats," BioMed Research International, 2019:4360525, pp. 1-11 Jan. 20, 2019.
UniProt Accession AOA2K3Z291_9STAP, *Staphylcoccus felis* Beta-class pehenol-soluble modulin, Gene C7J90_07630, Mar. 28, 2018, <https://www.uniprot.org/uniprot/AOA2K3Z291>.
Rodriquez, Kari, International Search Report and Written Opinion, PCT/US2022/013921, United States Patent & Trademark Office, Jun. 14, 2022.

* cited by examiner

*Primary Examiner* — Jennifer E Graser
(74) *Attorney, Agent, or Firm* — Gavrilovich, Dodd & Lindsey LLP

(57) ABSTRACT

This disclosure provides a synthesized version of *S. felis* C4 antimicrobial peptide as a topical antibiotic. *S. felis* C4 can be used as a probiotic strain of skin bacteria that can be transplanted onto the diseased skin of dogs, cats and dairy cows to outcompete and kill pathogenic bacteria that are causing infections such as bacterial pyoderma and mastitis.

9 Claims, 18 Drawing Sheets

Specification includes a Sequence Listing.

| Human species | # isolates | Sources |
|---|---|---|
| *S. aureus* | 1 | Skin |
| *S. hominis* | 1 | Skin |
| *S. capitis* | 1 | Skin |
| **Animal species** | **# isolates** | **Sources** |
| *S. pseudintermedius* | 17 | Skin |
| *S. felis* | 23 | Skin/perineum/nasal |
| *S. vitulinus* | 4 | Oral |
| *S. sciuri* | 6 | Oral/nasal |
| *S. xylosus* | 5 | Oral/nasal |
| *S. lentus* | 1 | Nasal |
| *S. fleuretti* | 1 | Nasal |
| *S. equorum* | 1 | Nasal |

| ANTIBIOTICS | MIC |
|---|---|
| Ampicillin | 0.047 |
| Erythromycin | 0.125 |
| Gentamicin | 0.064 |
| Rifampin | 0.006 |
| Tetracycline | 0.125 |
| Vancomycin | 1.5 |

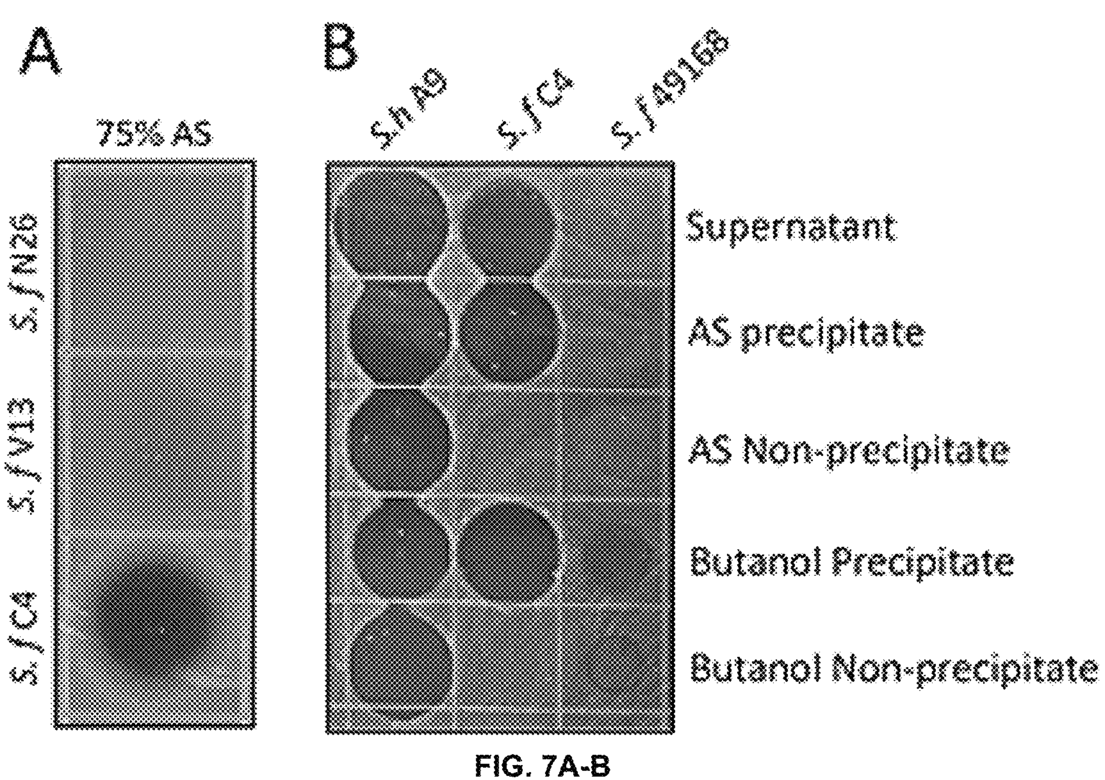
FIG. 7A-B
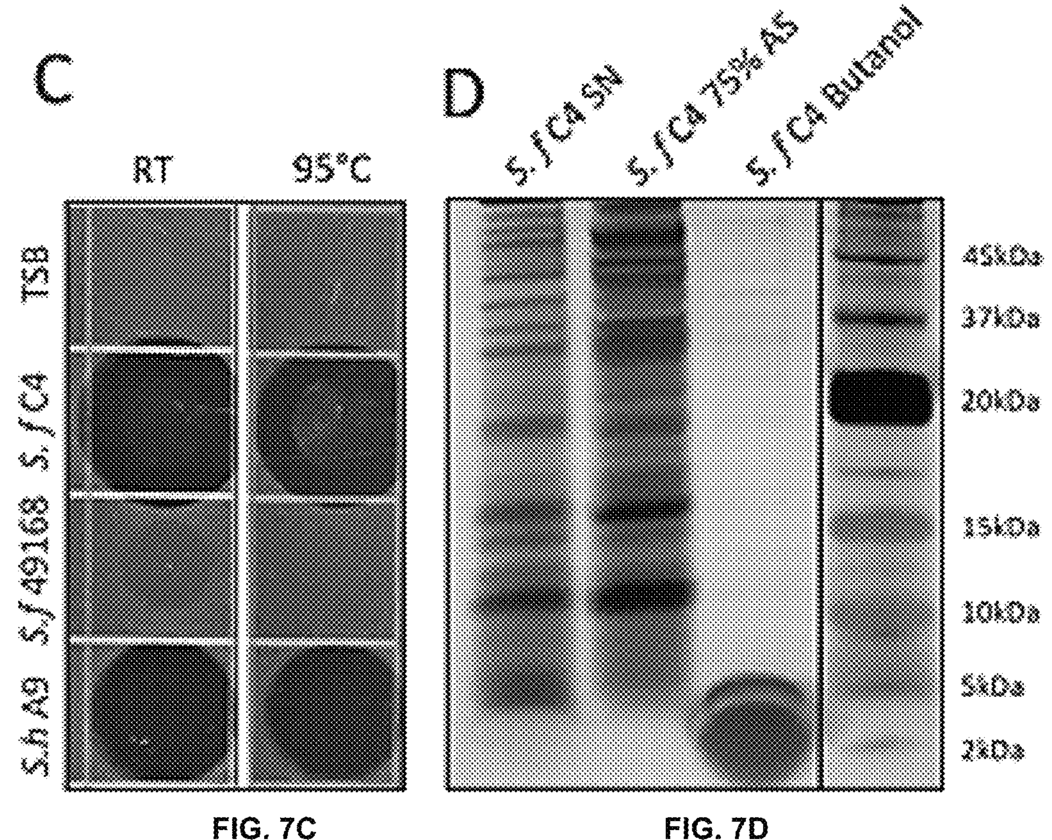
FIG. 7C
FIG. 7D

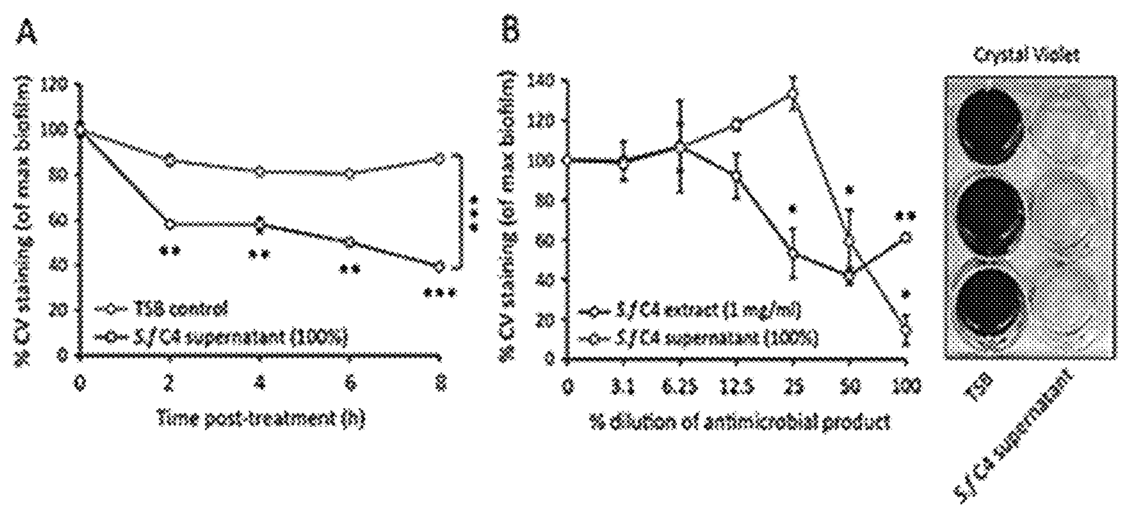
FIG. 8A
FIG. 8B
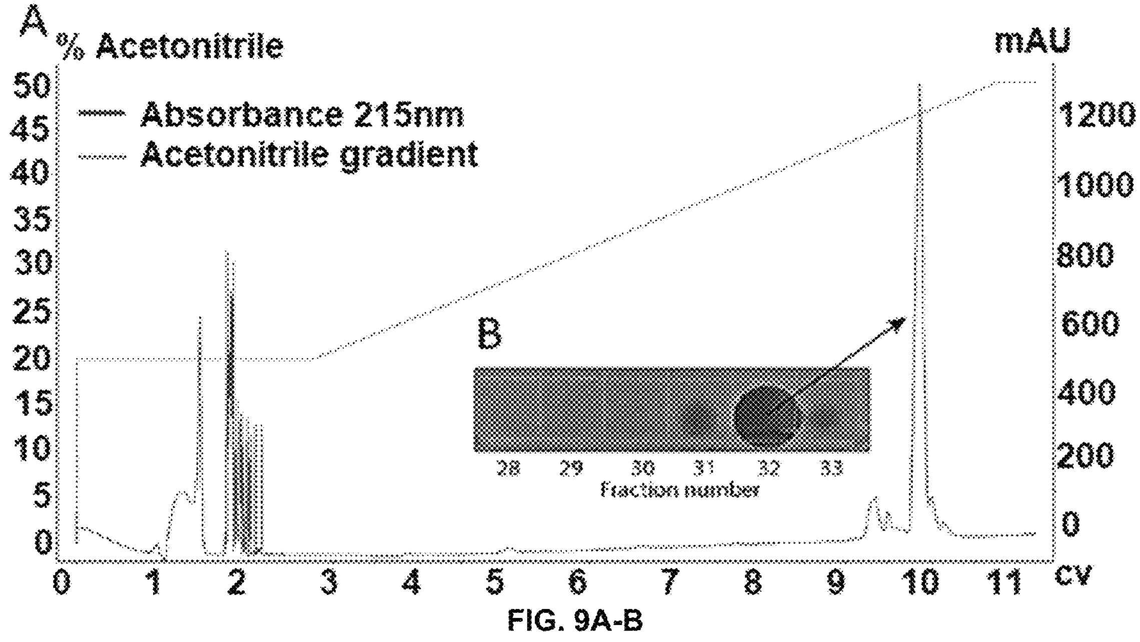
FIG. 9A-B
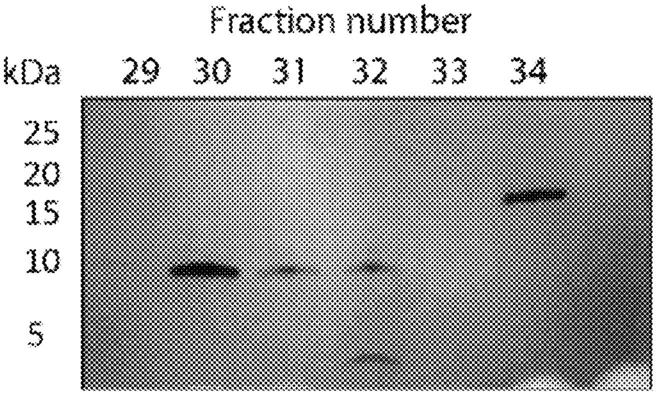
FIG. 9C

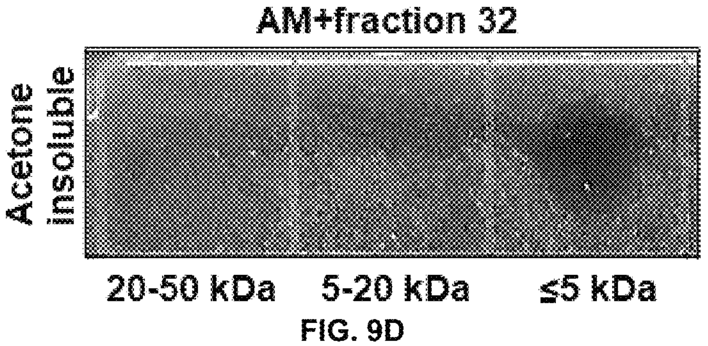

FIG. 9D

| Predicted protein | Accession | Amino acid sequence | Coverage | #Peptides | #PSMs | MW (kDa) | Non-active | Non-active | Active | Non-active |
|---|---|---|---|---|---|---|---|---|---|---|
| Complement inhibitor | [illegible] | [illegible] | [illegible] | [illegible] | [illegible] | [illegible] | [illegible] | [illegible] | [illegible] | [illegible] |
| PSMβ[illegible] | [illegible] | [illegible] | [illegible] | [illegible] | [illegible] | [illegible] | | [illegible] | [illegible] | |
| PSMβ[illegible] | [illegible] | [illegible] | [illegible] | [illegible] | [illegible] | [illegible] | [illegible] | [illegible] | [illegible] | [illegible] |
| PSMβ[illegible] | [illegible] | [illegible] | [illegible] | [illegible] | [illegible] | [illegible] | | [illegible] | [illegible] | |
| Unknown (EFhand) | [illegible] | [illegible] | [illegible] | [illegible] | [illegible] | [illegible] | [illegible] | [illegible] | [illegible] | [illegible] |
| [illegible]-like family | [illegible] | [illegible] | [illegible] | [illegible] | [illegible] | [illegible] | [illegible] | [illegible] | [illegible] | [illegible] |
| Acyl carrier protein | [illegible] | [illegible] | [illegible] | [illegible] | [illegible] | [illegible] | | [illegible] | [illegible] | |
| Delta hemolysin | [illegible] | [illegible] | [illegible] | [illegible] | [illegible] | [illegible] | | [illegible] | [illegible] | |

FIG. 9E

| | 1 … 10 … 20 … 30 … 40 … 50 | charge |
|---|---|---|
| *S. felis* C4 EF HAND | MSKLTRVVTSIMTVGFLTATLGLTAGNADAKLEGNGTLSQKQYQRLASQQF | +2.2 |
| *S. felis* C4 PSMβ1 | MSGLIDAIKTTVEAGLNGEWADMGLGIAEIVAKGIEAISGFFG.......... | -4.7 |
| *S. felis* C4 PSMβ2 | MSDLINAIKTTVEAGLNGEWTDMGFGIADIVAKGIDVILGFFG.......... | -4.7 |
| *S. felis* C4 PSMβ3 | MADLINAIKTTVEAGLNGEWTDMGFGIADIVAKGIDVISGFFG.......... | -4.7 |

FIG. 9F

ANTIMICROBIAL THERAPY

CROSS REFERENCE TO RELATED APPLICATIONS

This application is a U.S. National Phase Application filed under 35 U.S.C. § 371 and claims priority to International Application No. PCT/US2022/013921, filed Jan. 26, 2022, which application claims priority under 35 U.S.C. § 119 from Provisional Application Ser. No. 63/141,876, filed Jan. 26, 2021, the disclosures of which are incorporated herein by reference.

FIELD OF THE INVENTION

The disclosure relates to methods and compositions for treating infection, and modulating skin and mucosal microflora to treat diseases or disorders that are related to or exacerbated by dysbiosis.

BACKGROUND

Human and animal skin harbors commensal bacteria that generally live on the skin without causing harm. Many bacteria within the skin and mucosal microbiome produce antimicrobial peptides (AMPs) that do not damage the host but allow the bacteria to successfully outcompete others in the same niche. Certain bacteria colonizing healthy skin produce AMPs which effectively kill *Staphylococcus aureus*, a common cause of skin infection in humans and animals.

SUMMARY

Methicillin-resistant *Staphylococcus* pseudintermedius (MRSP) is an important emerging zoonotic pathogen that causes severe skin infections. To combat infections from drug-resistant bacteria, the transplantation of commensal antimicrobial bacteria as a therapeutic has shown clinical promise. A collection of diverse *staphylococcus* species from domestic dogs and cats were screened for antimicrobial activity against MRSP. A unique strain (*S. felis* C4) was isolated from feline skin that inhibited MRSP and multiple gram-positive pathogens. Competition experiments in mice showed that *S. felis* significantly reduced MRSP skin colonization and an antimicrobial extract from *S. felis* significantly reduced necrotic skin injury from MRSP infection. Fluorescence and electron microscopy revealed that *S. felis* antimicrobials disrupted bacterial but not eukaryotic cell membranes. LC/MS identified several *S. felis* phenol-soluble modulin beta (psmβ) peptides that exhibited antimicrobial and anti-inflammatory activity. These findings indicate a feline commensal bacterium that could be utilized in bacteriotherapy against difficult-to-treat animal and human skin infections.

*S. felis* C4 is a non-pathogenic strain of bacteria that kills other strains of bacteria. *S. felis* C4 does this by producing an antimicrobial peptide which targets other bacteria and causes their death. This disclosure provides for the use and composition of *S. felis* as a live or attenuated bacterial probiotic to kill bacteria causing skin infections. The disclosure also provides compositions and methods of using extracts of *S. felis* in formulations for the treatment of skin disease and disorders. The disclosure also provide a synthesised version of *S. felis* C4 antimicrobial peptide and the use of this product as a topical antibiotic.

The disclosure provides a composition comprising a thickened topical formulation of one or more probiotic bacterial strains and optionally, a prebiotic compound, a protectant, humectant, emollient, abrasive, salt, and/or surfactant; wherein the one or more probiotic bacterial strain comprises *S. felis*; and wherein the composition is formulated for the topical treatment of disorders of dysbiosis of the skin, scalp, or mucosae. In one embodiment, the one or more probiotic bacterial strain comprises *S. felis* C4. In another embodiment, the one or more probiotic bacterial strains is provided in a live form. In still another embodiment, the one or more probiotic bacterial strains is provided in a lyophilized or freeze-dried or spray dried form. In a further embodiment, the probiotic bacterial strain can be reconstituted into a live form. In still another or further embodiment of any of the foregoing, the composition comprises one or more peptides comprising sequences that are at least 90% identical to a sequence selected from SEQ ID NO:3, 4, 5, 6, 7, and 8.

The disclosure also provides a composition comprising a fermentation extract of *S. felis* C4. In one embodiment, the composition comprises one or more peptides comprising sequences that are at least 90% identical to a sequence selected from SEQ ID NO:3, 4, 5, 6, 7, and 8 and wherein the composition inhibits or kills *S. aureas* and/or *S. pseudintermidius*. In a further embodiment, the composition comprises peptides having one or more sequence selected from the group consisting of SEQ ID NO:3, 4, 5, and 6. In still another or further embodiment of any of the foregoing, the composition is a thickened topical formulation. In still another or further embodiment of any of the foregoing, the composition is prepared for application to a surface. In still another or further embodiment of any of the foregoing, the composition further comprises at least one antibiotic.

The disclosure provides a composition comprising one or more peptides comprising sequences that are at least 90% identical to a sequence selected from SEQ ID NO:3, 4, 5, 6, 7, and 8 and wherein the composition inhibits or kills *S. aureas* and/or *S. pseudintermidius*. In one embodiment, the composition is formulated as lotion, ointment cream, powder, unguent, oil, or spray.

The disclosure also provides a method for treating skin or mucosal infection in a subject comprising contacting the subject with an effective amount of a composition as described herein and above comprising an *S. felis*, extract or peptides derived therefrom. In one embodiment, the skin or mucosal infection comprises an infection by *S. aureas* and/or *S. pseudintermidius.*

The disclosure also provides a method of treating skin or mucosal infections in a mammal by applying to the skin or mucosa an effective amount of the composition described herein and above to a subject in need thereof. In one embodiment, the composition is applied topically. In another embodiment, the composition is formulated as a cream, ointment, unguent, spray, powder, oil, thickened formulation or poultice.

The disclosure provides a method of treating a bacterial infection in an animal or human, the method comprising exposing an infected area of the animal or human to a composition as described herein and above. In one embodiment, the bacterial infection is an infection by *S. aureas* and/or *S. pseudintermidius*. In another embodiment, the composition is in the form of a liquid formulation, ointment formulation, lotion formulation, cream formulation, gel formulation, liquid spray, lyophilized powder, lyophilized spray, mouth wash, or gargle. In still another embodiment, the composition is for the treatment of ear infections (e.g., Otitis externa), skin infections, or wound infections. In yet another embodiment, the compositions comprises a pure culture of *S. felis* C4. In a further embodiment, the *S. felis* C4 produces one or more peptides selected from the group consisting of SEQ ID NO:3, 4, 5, 6, 7 and 8. In another embodiment, the composition comprises about $10^6$ to $10^9$ cfu (colony forming units) per ml.

The disclosure provides a probiotic composition including a therapeutically effective concentration of a substantially pure culture of *S. felis* strain C4, said culture capable of producing one or more peptides having sequences selected from the group consisting of SEQ ID NO:3, 4, 5, 6, 7, 8 and conservative variants thereof upon fermentation in a nutrient medium. In one embodiment, the bacterial strain is included in a concentration of about $10^5$ to $10^9$ cfu (colony forming units) per ml of probiotic composition. In another embodiment, the composition is in the form of a cream, ointment, unguent, spray, powder, oil, thickened formulation or poultice.

Disclosed herein are compositions and methods for the treatment, amelioration, or prevention of one or more skin disorders or diseases associated with dysbiosis, especially dysbiosis of the skin, or symptoms thereof, or syndromes incorporating said disorders, diseases, or symptoms. Exemplary disorders or diseases to be treated according to the compositions and methods as disclosed herein include, but are not limited to, atopic dermatitis, eczema, pyotraumatic dermatitis, pyoderma, superficial pyoderma, folliculitis, rosacea, Netherton syndrome, acne, wounds (including abrasions, radiation damage, and burns), psoriasis, mastitis, icthyosis, lichen formation, and sebhorreic dermatitis, or any combination thereof. Exemplary symptoms of skin disorders or diseases associated with dysbiosis of the skin include but are not limited to thickened skin; discolored (especially reddish) skin; itching; open sores, blisters, cracks, or lesions that drain fluid, ooze, and/or crust; swelling; red rash or bumps; raw skin from scratching; red, leathery, cracked or scaly patches on the skin; dry, red patches, which may resemble a burn; burning, stinging or itching, which may be mild, moderate, or severe; small red, pus-filled bumps; yellowish scales or crust on the scalp, ears, face or other parts of the body; dandruff; icthyosis, dermal fibrosis, or other symptoms of localized, persistent inflammation or of dermatitis or dermatitis syndromes as are known in the art or any combination thereof. Representative dermatitis syndromes and/or symptoms thereof for which administration of the compositions described herein, preferably according to the methods described herein may comprise one or more of hyper IgE syndrome, pneumatocele, hyperextensibility, osteopenia, aneurysma, hypertension, recurrent infections, Wiskott-Aldrich syndrome, thrombocytopenia, recurrent infections, ectodermal dysplasias, Netherton syndrome, erythroderma, peeling skin disease, hyperhidrosis, clubbing, photophobia, severe dermatitis, multiple allergies, and metabolic wasting (SAM) syndrome, recurrent infections, multiple allergies, ichthyosis follicularis, alopecia, and photophobia (IFAP) syndrome, ichthyosis follicularis, alopecia, and photophobia; minimal change nephrotic syndrome (MCNS); SAM, severe dermatitis, multiple allergies, atopic dermatitis with ichthyosis follicularis, ichthyosis follicularis, atrichia, and/or photophobia, and/or any combination thereof. In some embodiments, the compositions and methods of the disclosure provide a treatment for atopic dermatitis.

In some embodiments, the compositions and methods of the disclosure contemplate treatments for diseases or disorders related to dysbiosis of the skin. In some embodiments, the disclosure contemplates treatment, amelioration, or cure of the underlying dysbiosis. In some embodiments, said dysbiosis comprises a reduction or decrease in the relative amount or the absolute amount of a beneficial, protective, or health-associated bacterium in, on, or associated with the skin or external mucosae or the normal flora associated therewith. In some embodiments, said dysbiosis may comprise colonization, infection, overgrowth, or an increase in the presence, relative amount, or absolute amount of a deleterious, infectious, pathogenic, or disease-associated bacterium. In some embodiments, said deleterious, infectious, pathogenic, or disease-associated bacterium may comprise one or more bacteria known in the art to cause or to be associated with infections, diseases, disorders, or pathological conditions, especially inflammations and irritations, of the skin and/or external mucosae. In some embodiments, said deleterious, infectious, pathogenic, or disease-associated bacterium may comprise one or more of *Staphylococcus aureus, Staphylococcus schleiferi, Staphylococcus intermedius, Staphylococcus pseudintermedius, Staphylococcus felis*, or other bacterial infections such as *Mallassezia*, especially *Mallassezia sympodialis, Mallassezia globosa, Micrococcus* spp., *Acinetobacter* spp., alpha-hemolytic streptococci, and/or other pathogens of the skin or external mucosa. In some embodiments, the deleterious, infectious, pathogenic, or disease-associated bacterium is *S. aureas* and/or *S. pseudintermidius.*

The compositions disclosed herein may comprise an active drug substance or an active cosmetic substance wherein said active drug substance or active cosmetic substance has the effect of ameliorating or curing dysbiosis in a tissue or at a particular location in a subject. The effect of ameliorating or curing dysbiosis in a tissue or at a particular location in a subject may comprise any of the steps of reducing the presence, activity, or virulence of a pathogen, an overgrown bacterium, or a disease-associated bacterium; increasing the presence activity, or beneficial effects of a commensal, beneficial, or health-associated bacterium; enhancing the stability of a bacterial community; altering the production, secretion, or availability of one or more metabolites; altering the utilization of a food source, electron acceptor, electron donor, ion or counterion; or any other action which may alter the status of the flora or microbiota of a subject, especially where such alteration has an effect on the health, appearance, or comfort of the subject.

The compositions disclosed herein may comprise one or more forms intended for administration to a subject, especially by topical administration. In some embodiments, a topical formulation disclosed herein can be in a form selected from the group consisting of liquid, including solution and suspension, solid, foamy material, emulsion, paste, gel, cream, and a combination thereof, such as a liquid containing a certain amount of solid contents. In some embodiments, the flavoring concentrate formulation may be a fluid, gel, or thickened form which may be aqueous-based or nonaqueous-based. In some embodiments, the compositions disclosed herein may comprise an oil. In some embodiments, the compositions disclosed herein may comprise a lotion. In some embodiments, the compositions disclosed herein may comprise a mist, spray, rinse, liquid, solid stick, roll-on, powder, or other composition as is known in the art or reasonably could be utilized for the administration of active drug compounds to sites of inflammation and/or infection on the skin.

The compositions of the disclosure may comprise, in some embodiments, an extract, lysate, growth medium, conditioned growth medium, or active isolate thereof, from

*S. felis* bacterial cells. One of ordinary skill could readily isolate an extract, lysate, growth medium, conditioned growth medium, or active isolate thereof, from *S. felis* bacterial cells using any suitable method known in the art. In one non-limiting example, the bacterial cell can be disrupted by mechanical means. The resulting lysate or suspension may then be processed to remove undesired solids. The isolate may then be placed in a shallow vessel and quickly exposed to low temperature, i.e., flash frozen, for example at −20° C. or lower, preferably under a vacuum for removal of water content (lyophilization). In some embodiments, this process is carried out with a bacterial cell population. In some embodiments, this process is carried out with a bacterial cell lysate. In some embodiments, this process is carried out with a bacterial growth medium.

The details of one or more embodiments of the invention are set forth in the accompanying drawings and the description below. Other features, objects, and advantages of the invention will be apparent from the description and drawings, and from the claims.

Figure 1A:
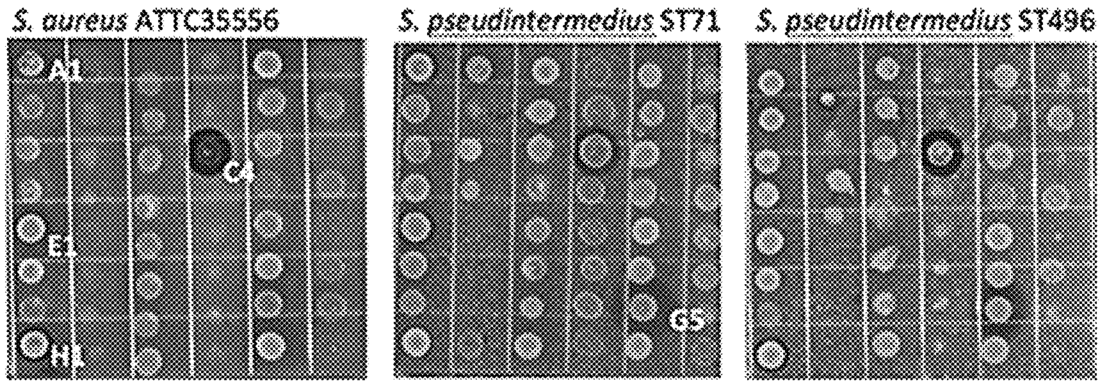
FIG. 1A-C shows (A) Radial diffusion assay for antimicrobial activity against the human pathogen, *S. aureas* and four isolates of the veterinary pathogen, *S. pseudintermedius*. Each dot represents 10 ul of a broth culture of animal derived staphylococci inoculated onto an agar culture of each respective pathogen. All isolates were inhibited by the positive control *S. hominis* A9 (H1) and *S. felis* C4, and were variably inhibited by *S. pseudintermedius* isolates A1 and E1 and *S. felis* isolates A2, F2 and G5. (B) *S. aureas* growth (OD600) after 24 hr incubation in 10% conditioned media from animal-derived staphylococci that showed inhibitory activity on the radial diffusion assay. (C) Radial diffusion assay of 50% and 70% saturated ammonium sulphate precipitated conditioned media from *S. felis* isolates A2, C4 and G5 against *S. aureas*.
Figure 1A:
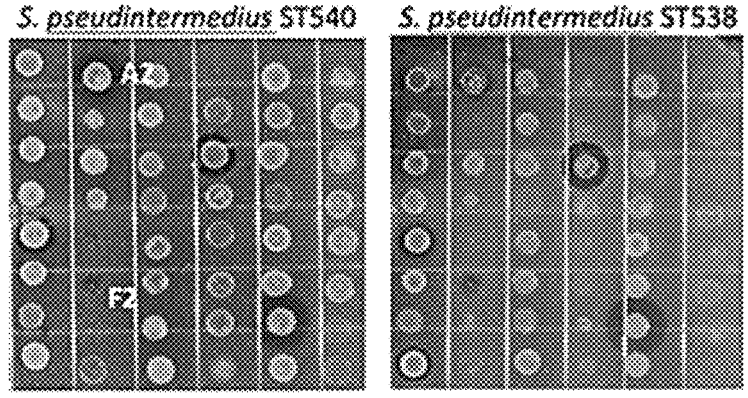

FIG. 7A-D Generation of a partially purified antimicrobial extract from *S. felis* C4. (A) Supernatant of indicated antimicrobial *S. felis* strains (S. f C4, N26, V13) were incubated with 75% ammonium sulfate (AS) and the resulting precipitate was inoculated onto agar containing *S. pseudintermedius* ST71, to determine antimicrobial activity. (B) Supernatant of *S. felis* C4, positive-control *S. hominis* A9, or negative-control *S. felis* ATCC 49168 was extracted in 75% AS or 25% n-butanol and activity of the precipitate and non-precipitate fractions were assayed against *S. pseudintermedius* ST71. (C) Supernatant of *S. felis* C4 (S. f C4), *S. hominis* A9 (S. h A9), *S. capitis* E12 (S. c E12) or TSB alone, were maintained at room temperature (RT) for 1 week or boiled at 95° C., for 30 mins and activity determined by inoculation directly onto agar containing *S. pseudintermedius* ST71. (D) Total protein silver stain of *S. felis* C4 supernatant before precipitation or after precipitation in 75% AS or 25% butanol.

FIG. 8A-B shows *S. felis* C4 supernatant and extract disrupt *S. pseudintermedius* biofilm. (A) Decrease in crystal violet staining of a 4 h preformed *S. pseudintermedius* ST71 biofilm during 8 h incubation with 100% *S. felis* C4 sterile supernatant. (B) Decrease in crystal violet staining of a 4 h preformed *S. pseudintermedius* ST71 biofilm after 24 h incubation with serially diluted *S. felis* C4 sterile supernatant (100%) or *S. felis* C4 extract (1 mg/ml). Right inset is a representative image of crystal violet staining after incubation with 100% *S. felis* C4 supernatant. (A-B) Error bars indicate SEM. Representative of two separate experiments. A two-tailed, unpaired Student's t test was performed. p values: *$p<0.05$; $p<0.01$; *$p<0.001$.

FIG. 9A-G shows HPLC purification yields antimicrobial fraction from *S. felis* C4 supernatant. (A) Reverse-phase high-performance liquid chromatography (HPLC) elution profile from sterile supernatant of *S. felis* C4 strain loaded onto a C8 column. (B) Inset image of antimicrobial activity exhibited by fraction 32 against *S. pseudintermedius* ST71 corresponding to the indicated peak. (C) Silver stain of total protein content in the different fractions indicated. (D) Radial diffusion assay of antimicrobial activity of the AM+ fraction 32 after extraction and acetone precipitation of proteins within different sized silver stain gel fragments. (E) Mass spectrometry (MS) table of the top 8 peptide hits obtained from HPLC fractions that were active (fraction 32) or inactive (26, 30, 36) against *S. pseudintermedius* ST71. (F) ClustalW multiple amino acid sequence alignment of all three *S. felis* C4 genetically-encoded PSMβ peptides with predicted net charge at pH 7.4 (Prot pi) and amino acid sequence of a EF-hand domain-containing peptide with unknown function. (G) Alpha helical wheel plots of *S. felis* C4 PSMβ1-3, EF-hand domain peptide and human LL-37 peptide, indicating conserved α-helical, amphipathic-like structures with indicated hydrophobic yellow residues confined to one side (indicated by arrow) and grey hydrophilic residues on the opposing side.

Figures 9G, 10:
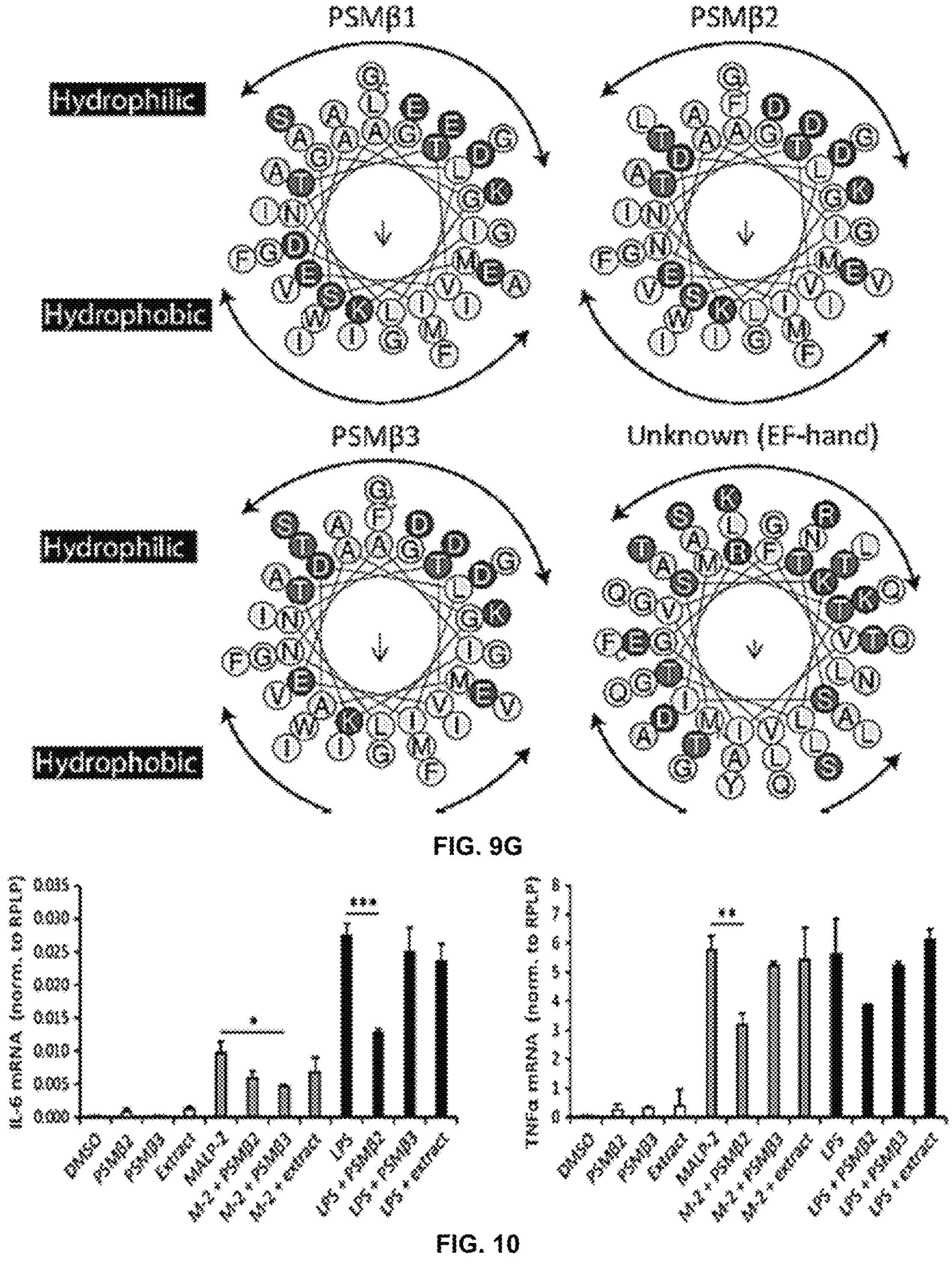

FIG. 10 shows PSMβ2 reduces TLR2- and TLR4-stimulated transcripts in THP-1 macrophages. Transcript abundance of inflammatory cytokines IL-6 and TNFα in THP-1 cells stimulated with or without TLR2/6 agonist MALP-2 (200 ng/ml) or TLR4 agonist LPS (1 μg/ml) in the presence or absence of *S. felis* C4 extract, PSMβ2 or PSMβ3 (10 μg/ml) or DMSO control (0.1%) 4 h post-treatment. Error bars indicate SEM. One-way ANOVA with multiple corrections (Turkey correction) was performed. p values: * $p<0.05$; , $p<0.01$; * $p<0.001$.

Figure 11A:
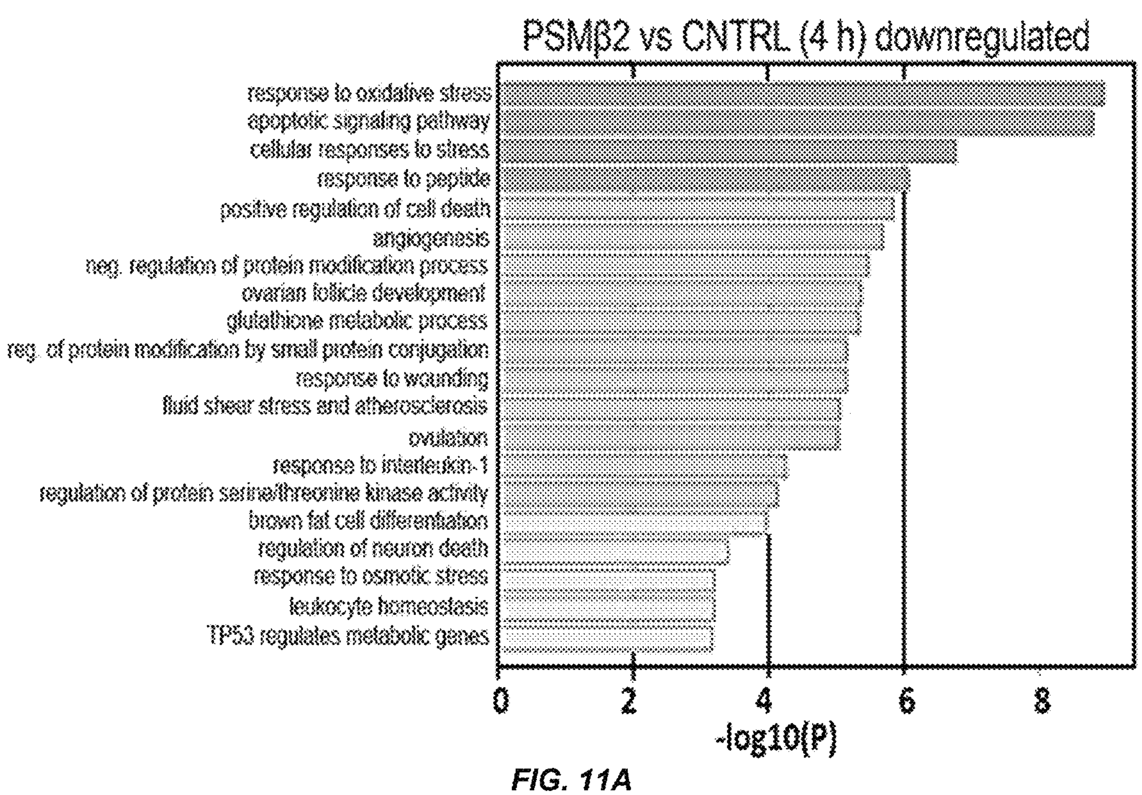
Figure 11B:
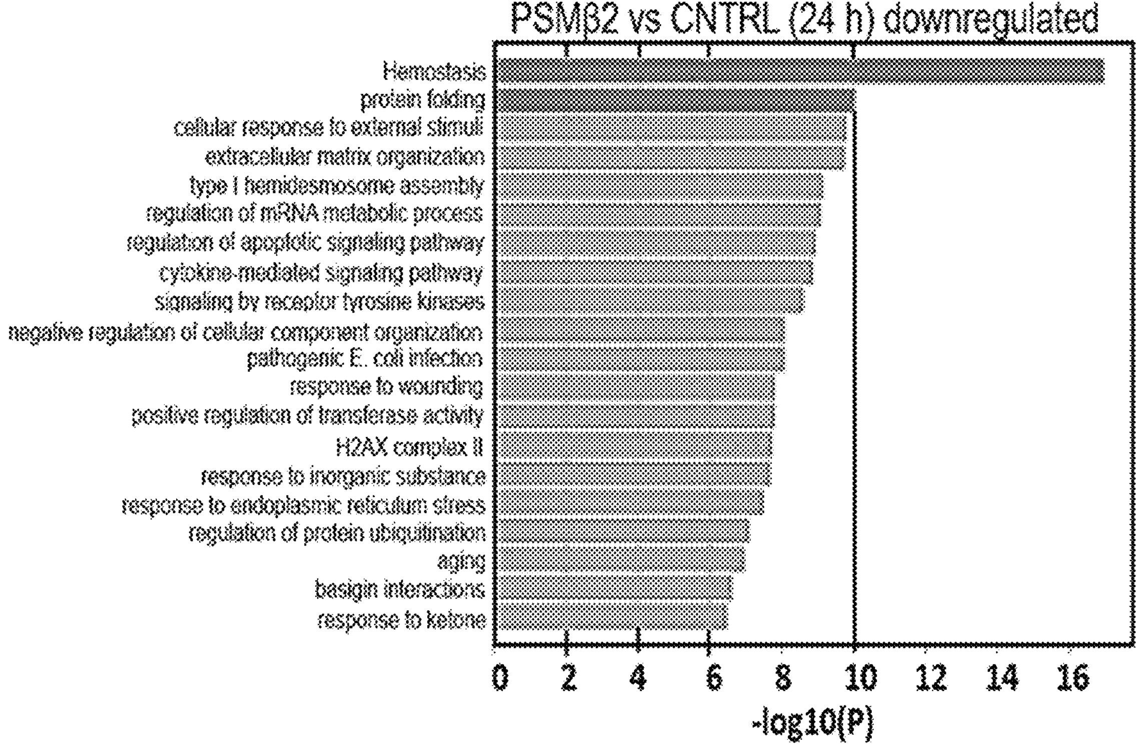

FIG. 11A-B shows PSMβ2 suppresses TLR3-mediated cellular activation and downregulates responses to bacterial pathogens. (A-B) GO pathway analysis of genes downregulated in NHEKs at 4 h (A) and 24 h (B) after treatment with PSMβ2 versus DMSO control.

DETAILED DESCRIPTION

As used herein and in the appended claims, the singular forms "a," "an," and "the" include plural referents unless the context clearly dictates otherwise. Thus, for example, reference to "an agent" includes a plurality of such agents and reference to "the cell" includes reference to one or more cells and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. With respect to any term that is presented in one or more publications that is similar to, or identical with, a term that has been expressly defined in this disclosure, the definition of the term as expressly provided in this disclosure will control in all respects.

The disclosure provides evidence that the community of bacteria residing on animal skin provides an important shield against infection. Without intending to be bound by any particular theory, dysfunction in this microbiome-mediated antimicrobial defense system may enable colonization of the skin by pathogenic microorganisms leading to various skin/coat conditions. This observation suggests that strategies of bacteriotherapy of the skin may be useful as a method to suppress infection without use of pharmaceutically derived antibiotics.

"Active" or "activity" as used herein with reference to a biological entity refers to a biological activity of a native or naturally-occurring probiotic molecule, or an engineered variant thereof, wherein "biological" activity refers to a biological function (either inhibitory or stimulatory) caused by the biological entity such as a probiotic molecule. A biologically active probiotic composition will comprise a bacterial population that produces one or more agent(s) that modulate pathogen growth on a surface including a skin surface.

The term "antimicrobial" as used herein refers to a killing or inhibitory activity of an agent (e.g., probiotic, commensal bacteria, bacterial extract, peptides etc.) that destroys, or inhibits or prevents the growth or proliferation of, a microbe (e.g., a bacterium, fungus, and/or virus).

An "antimicrobial composition" as used herein refers to a composition comprising a population of bacterial organisms or extract thereof that can inhibit or kill a different species of bacterial organism upon contact. For example, *S. felis* C4 is a non-pathogenic strain of bacteria that kills other strains of bacteria. *S. felis* C4 does this by producing an antimicrobial peptide which targets other bacteria and causes their death. Accordingly, an antimicrobial composition can comprise *S. felis* C4, extracts of *S. felis* C4, and/or substantially purified polypeptide(s) derived from or synthesized that correspond to the antimicrobial peptide(s) that are produced by *S. felis* C4. This disclosure provides for the use and composition of *S. felis* as a live or attenuated bacterial probiotic to kill bacteria causing skin infections. The disclosure also provides compositions and methods of using extracts of *S. felis* in formulations for the treatment of skin disease and disorders. The disclosure also provide a synthesised version of *S. felis* C4 antimicrobial peptide and the use of this product as a topical antibiotic or antimicrobial agents for surface applications.

The terms "apply" and or "application," as used herein in reference to a composition of the disclosure refers to contacting a surface, including a mammalian skin surface, with a topical composition of the disclosure.

The term "dermatologically acceptable" as used herein refers to a composition or component thereof that may be used in contact with mammalian skin tissue without undue toxicity, incompatibility, instability, allergic response, and the like. The term "dermatologically acceptable carrier" as used herein refers to a carrier that is suitable for topical application to keratinous tissue, has acceptable aesthetic properties, is compatible with the active compounds, and does not cause any safety or toxicity concerns.

By "derived," is meant that a probiotic molecule is either directly or indirectly produced by a probiotic bacteria of the disclosure. For example, a probiotic bacteria may secrete the probiotic molecule directly into the culture medium.

As used herein, "dysbiosis" means an imbalance or maladaptation of the flora or microbiota within one or more tissues, compartments, subcompartments, or locations of the body, and particularly within the various domains and subdomains of the skin. Such dysbiosis is characterized by a change in the composition of the local microbiome, in terms of the species/strains which are present and/or the relative abundance or proportion of the species/strains which are present, in which the change has a definable effect on the host organism. The effect on the host organism can result from microbiome-mediated changes in electrolyte balance, biofilm formation, epithelial, mesothelial, or endothelial barrier integrity, or the release from the microbiome of metabolites which directly (e.g., as toxins or effectors) or indirectly (e.g., as pre-cursors to toxins or effectors) affect the health, appearance, or comfort of the host.

"Host cells" encompassed by of the disclosure are any cells in which a polynucleotide of the disclosure can be used to express a polypeptide, peptide, derivatives or variants of the disclosure. The term also includes any progeny of a host cell. Host cells, which are useful, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein. In one embodiment, a host cell can be a bacterial cell present in a normal bacterial flora of the skin that has been engineered to express or over express a peptide or other antimicrobial peptide of the disclosure. These engineered bacterial cells can then be used as a probiotic such that they can be applied to the skin.

Host cells can be eukaryotic host cells (e.g., mammalian cells). In one embodiment, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g., cytokines, clotting factors, and antibodies (Brasel et al., Blood 88:2004 2012 (1996); Kaufman et al., J. Biol Chem 263: 6352 6362 (1988); McKinnon et al., J Mol Endocrinol 6:231 239 (1991); Wood et al., J. Immunol 145:3011 3016 (1990)). The dihydrofolate reductase (DHFR)-deficient mutant cell lines (Urlaub et al., Proc Natl Acad Sci USA 77:4216 4220 (1980)) are the CHO host cell lines commonly used because the efficient DHFR selectable and amplifiable gene expression system allows high level recombinant protein expression in these cells (Kaufman, Meth Enzymol 185:527 566 (1990)). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

"Isolated" refers to a molecule that has been purified from its source or has been prepared by recombinant or synthetic methods and purified. Purified probiotic molecules are substantially free of other amino acids. Similarly, isolated polynucleotides are polynucleotides that have been removed from the natural environment (e.g., have been removed from naturally occurring sequences at the 5' and or 3' ends). Isolated and purified are used interchangeably herein. The term "isolated" as used herein can refer to a polynucleotide that is substantially free of proteins, lipids, and other polynucleotides with which an in vivo-produced polynucleotides naturally associated. Typically, the polynucleotide is at least 70%, 80%, or 90% isolated from other matter, and conventional methods for synthesizing polynucleotides in vitro can be used in lieu of in vivo methods.

"Percent sequence identity" is defined herein as the percentage of amino acid residues (or nucleic acid bases) in the candidate sequence that are identical with the residues (or bases) in the sequence of interest after aligning the sequences and introducing gaps, if necessary, to achieve the maximum percent sequence identity, and not considering any conservative substitutions as part of the sequence identity. None of 5', 3', or internal extensions, deletions or insertions into the candidate sequence shall be construed as affecting sequence identity or homology. Methods and computer programs for the alignment are well known in the art, such as "BLAST".

As used herein, "polynucleotide" refers to a polymer of deoxyribonucleotides or ribonucleotides, in the form of a separate fragment or as a component of a larger genetic construct (e.g., by operably linking a promoter to a polynucleotide encoding a peptide of the disclosure). Numerous genetic constructs (e.g., plasmids and other expression vectors) are known in the art and can be used to produce a polypeptide or peptide of the disclosure in cell-free systems or prokaryotic or eukaryotic (e.g., yeast, insect, or mammalian) cells. By taking into account the degeneracy of the genetic code, one of ordinary skill in the art can readily synthesize polynucleotides encoding a polypeptide or peptide of the disclosure. The polynucleotides of the disclosure can readily be used in conventional molecular biology methods to engineer, clone or produce a polypeptide or peptide of the disclosure.

Although the genetic code is well understood by one of skill in the art and it is routine in generating polynucleotides encoding a desired polypeptide sequence; the disclosure also provides polynucleotides encoding the polypeptides expressed from *S. felis* C4.

A "protein" or "polypeptide", which terms are used interchangeably herein, comprises one or more chains of chemical building blocks called amino acids that are linked together by chemical bonds called peptide bonds. Peptides generally refer to shorter segments of amino acid polymers (e.g., 2-10, 10-20, 20-30 amino acids), while polypeptides generally refer to longer amino acid polymers (e.g., greater than 30 amino acids). The terms peptides and polypeptides can be used interchangeably herein.

Polynucleotides encoding the polypeptide and peptides of the disclosure can be isolated from a cell (e.g., a cultured cell), or they can be produced in vitro. A DNA sequence encoding a peptide of interest can be obtained by: 1) isolation of a double-stranded DNA sequence from genomic DNA; 2) chemical manufacture of a polynucleotide such that it encodes the peptide of interest; or 3) in vitro synthesis of a double-stranded DNA sequence by reverse transcription of mRNA isolated from a donor cell (i.e., to produce cDNA). Among the standard procedures for isolating cDNA sequences of interest is the formation of plasmid or phage containing cDNA libraries that are derived from reverse transcription of mRNA in donor cells that have a high level of genetic expression. When used in combination with polymerase chain reaction technology, even rare gene products can be cloned.

Any of various art-known methods for polypeptide, peptide and protein purification can be used to isolate a polypeptide, peptide or protein of the disclosure. For example, preparative chromatographic separations and immunological separations (such as those employing monoclonal or polyclonal antibodies) can be used. Carrier peptides can facilitate isolation of fusion proteins that include the peptides of the disclosure. Purification tags can be operably linked to a peptide of the disclosure. For example, glutathione-S-transferase (GST) allows purification with a glutathione agarose affinity column. When either Protein A or the ZZ domain from *Staphylococcus aureus* is used as the tag, purification can be accomplished in a single step using an IgG-sepharose affinity column. The pOprF-peptide, which is the N-terminal half of the *P. aeruginosa* outer membrane protein F, can readily be purified because it is the prominent protein species in outer membrane preparations. If desired, fusion peptides (e.g., comprising a purification domain and a domain of interest) can be purified using reagents that are specifically reactive with (e.g., specifically bind) the peptide of the fusion peptide. For example, monoclonal or polyclonal antibodies that specifically bind the peptide can be used in conventional purification methods. Techniques for producing such antibodies are well known in the art.

A fusion construct comprising a polypeptide linked to a peptide of the disclosure can be linked at either the amino or carboxy terminus of the peptide. Typically, the polypeptide that is linked to the peptide is sufficiently anionic such that the peptide has a net charge that is neutral or negative. The anionic polypeptide can correspond in sequence to a naturally occurring protein or can be entirely artificial in design. Functionally, the polypeptide linked to a peptide (the "carrier polypeptide") may help stabilize the peptide and protect it from proteases, although the carrier polypeptide need not be shown to serve such a purpose. Similarly, the carrier polypeptide may facilitate transport of the fusion peptide. Examples of carrier polypeptides that can be utilized include anionic pre-pro peptides and anionic outer membrane peptides. Examples of carrier polypeptides include glutathione-S-transferase (GST), protein A of *Staphylococcus aureus*, two synthetic IgG-binding domains (ZZ) of protein A, outer membrane protein F of *Pseudomonas aeruginosa*, protein transduction domains and the like. The disclosure is not limited to the use of these polypeptides; others suitable carrier polypeptides are known to those skilled in the art. In another aspect, a linker moiety comprising a protease cleavage site may be operably linked to a peptide or variant of the disclosure. For example, the linker may be operable between to domains of a fusion protein (e.g., a fusion protein comprising a peptide and a carrier polypeptide). Because protease cleavage recognition sequences generally are only a few amino acids in length, the linker moiety can include the recognition sequence within flexible spacer amino acid sequences, such as GGGGS (SEQ ID NO: 1). For example, a linker moiety including a cleavage recognition sequence for Adenovirus endopeptidase could have the sequence GGGGGGSMFGGAKKRSGGGGGG (SEQ ID NO: 2). If desired, the spacer DNA sequence can encode a protein recognition site for cleavage of the carrier polypeptide from the peptide. Examples of such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at methionine or related residues. In addition, the fused product can be cleaved by insertion of a codon for tryptophan (cleavable by o-iodosobenzoic acid) or glutamic acid (cleavable by *Staphylococcus* protease). Insertion of such spacer DNA sequences is not a requirement for the production of functional peptides, such sequences can enhance the stability of the fusion peptide. The pre-pro defensin sequence is negatively charged, so accordingly, it is envisioned within the disclosure that other DNA sequences encoding negatively charged peptides also can be used as spacer DNA sequences to stabilize the fusion peptide.

As used herein, "probiotic" refers to the process of providing live or attenuated microbial cultures, or lysates, lyophiles or extracts of such cultures, in order to supplement or replace elements of a cutaneous or mucosal flora. An attenuated microbe for delivery to the skin can be a bacteria that has been genetically modified to (a) make the bacterial vector non-pathogenic, (b) have reduced pathogenicity, (c) be replication defective, or (d) to be non-antigenic. Other attenuation are known in the art. The attenuation is typically performed by knocking out a gene or disrupting a gene coding sequence or expression control element such that the attention of (a)-(c) or (d) is accomplished. Such techniques are known in the art and numerous such attenuated bacterial and viral vectors are known.

The term "purified" as used herein refers to a peptide or polynucleotide that is substantially free of other proteins, lipids, and polynucleotides (e.g., cellular components with which an in vivo produced peptide or polynucleotide would naturally be associated). Typically, the peptide is at least 70%, 80%, or most commonly 90% pure by weight. As described more fully below, the composition can further comprise a cathelicidin peptide or derivative thereof.

As used herein an "*S. felis* antimicrobial peptide" refers to one or more peptides selected from the group consisting of (SEQ ID NO is in parenthesis):

```
PSMβ1:
                                              (3)
Formyl-MSGLIDAIKTTVEAGLNGEWADM
GLGIAEIVAKGIEAISGFFG

PSMβ2:
                                              (4)
Formyl-MSDLINAIKTTVEAGLNGEWTDM
GFGIADIVAKGIDVILGFFG

PSMβ2:
                                              (5)
Non-Formyl-MSDLINAIKTTVEAGLNGE
WTDMGFGIADIVAKGIDVILGFFG

PSMβ3:
                                              (6)
Formyl-MADLINAIKTTVEAGLNGEWTDM
GFGIADIVAKGIDVISGFFG
```

And may optionally include peptides of SEQ ID NO:7 and/or 8.

The term "subject" as used herein refers to any member of the animal kingdom, including birds, fish, invertebrates, amphibians, mammals, and reptiles. Typically, the subject is a human or non-human vertebrate. Non-human vertebrates include livestock animals, companion animals, and laboratory animals. Non-human subjects also specifically include non-human primates as well as rodents. Non-human subjects also specifically include, without limitation, poultry, chickens, horses, cows, pigs, goats, dogs, cats, guinea pigs, hamsters, mink, rabbits, crustaceans, and molluscs. Typically the subject is poultry or a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

The term "topical composition" as used herein refers to a composition suitable for application to mammalian, e.g., human, skin. Non-limiting examples of topical compositions include skin care formulations such as cleansers (e.g., liquid, bar, gel, oil, or foam), toners, serums, masks, lotions, creams, ointments, balms, oils, scrubs, and treatments; as well as cosmetic products. Topical compositions optionally regulate and/or improve various skin conditions or treat an infection, disease or disorder resulting from dysbiosis.

A "variant" refers to an agent that differs in structure by retains at least one biological activity associated with the agent from which is it derived or engineered. For example, a variant is an antimicrobial peptide (e.g., a peptide of the disclosure) that is an altered form of a referenced antimicrobial peptide. For example, the term "variant" includes an antimicrobial peptide produced by the method disclosed herein in which at least one amino acid (e.g., from about 1 to 10 amino acids) of a reference peptide is substituted with another amino acid. Derivatives can be produced by adding one or a few (e.g., 1 to 5) amino acids to an antimicrobial peptide without completely inhibiting the antimicrobial activity of the peptide. In addition, C-terminal derivatives, e.g., C-terminal methyl esters, can be produced and are encompassed by the disclosure. A variant of the sequences described herein are biologically active sequences that have a peptide sequence that differs from the sequence of a native or wild-type sequence, by virtue of an insertion, deletion, modification and/or substitution of one or more amino acids within the native sequence. Such variants generally have less than 100% sequence identity with a native sequence. Ordinarily, however, a biologically active variant will have an amino acid sequence with at least about 70% sequence identity with the sequence of a corresponding naturally occurring sequence, typically at least about 75%, more typically at least about 80%, even more typically at least about 85%, even more typically at least about 90%, and even more typically of at least about 95%, 96%, 97%, 98%, or 99% sequence identity.

Skin is colonized by hundreds of diverse bacterial species that exist within a complex and dynamic chemical landscape. These chemical interactions can play important roles in skin health, immune education and protection against pathogen colonization and infection. The composition of the skin microbial community of humans and animals varies extensively, in part due to different skin habitats, i.e. increased hair density in animals, as well as more subtle differences in the chemical and biological conditions of the skin. Overall, the human microbial skin community is distinct from and significantly less diverse than that of both wild and domestic animals. Human skin is generally dominated by few taxa present at high abundance, e.g., cutibacteria, streptococci and staphylococci, whereas canine skin harbors a more equally distributed and diverse group of taxa. Naturally, close contact between humans and animals can be a source for microbial transmission. Although it remains to be determined if shared taxa are stable over time, there are reports that exposure to pets early in life can be protective against atopic disease in later life.

Moreover, subjects with diseased skin, such as those with atopy, demonstrate a different array of bacterial species in their commensal skin microbiome compared to patients with healthy skin. Not only is the microbiome of healthy skin qualitatively different to atopic skin in the array of bacterial species present, but functional differences exist between the microbiome of healthy and diseased skin. Bacterial antimicrobial peptide (AMP) production is deficient in atopic patients compared to healthy individuals, which may be one reasons why atopic patients are predisposed to *S. aureas* infections. Skin microbial communities vary within anatomical sites in an individual but individuals in the same household, community, and species have more commonalities in their skin microbiome with others from their own group than with outgroups. Sharing of skin microbiota is not limited to cohabiting humans; it is also seen between humans and pets in the same household.

There are also many documented cases of human staphylococcal infection from epidemiological exposure to dogs. Companion animals can act as reservoirs for methicillin-resistant *S. aureas* (MRSA) and more commonly, *S. pseudintermedius* (MRSP), with both species sharing many common invasion and virulence factors. The zoonotic significance of *S. pseudintermedius* may have been previously underestimated because it was frequently misidentified as *S. aureas* in human wound infections. More advanced diagnostic techniques such as MALDI-TOF have led to increased detection of human *S. pseudintermedius* infections. Colonization of *S. pseudintermedius* is a contributing factor in canine atopic dermatitis (AD). *S. pseudintermedius* is one of the most common pathogens isolated from the skin of dogs and becoming increasingly prevalent on humans. The incidence of severe and recurrent infections in animals and humans caused by methicillin-resistant *S. pseudintermedius* is increasing and is associated with a predominant clone belonging to the multi-locus sequence type ST71. ST71 isolates exhibit resistance to many classes of antibiotics and represent a considerable therapeutic challenge.

Interestingly, the prevalence of AD in humans and AD in dogs are similar (10-15% in US) and present with remarkably similar immunological and clinical manifestations. Likewise, several studies have reported a decrease in the microbiome diversity of AD and increased colonization of *S. aureas* in humans and *S. pseudintermedius* in dogs. In human AD, *S. aureas* was identified in higher relative abundances during disease flares. Similarly, the relative abundance of *S. pseudintermedius* was also shown to increase with disease flares in canine AD. Common treatment modalities exist for both diseases. Dilute bleach baths are a common antiseptic treatment for AD, with the goal of reducing the carriage of staphylococci. However, its effectiveness as an antibacterial agent is controversial, in part, because these existing antibiotic therapies non-specifically kill bacteria, which impacts the homeostasis of the resident microflora. Imbalanced microflora contribute to the pathogenesis of skin inflammatory diseases.

Atopic skin disorders are often associated with a dysfunction of the epidermal barrier and relapsing skin inflammation. The severity of this disease is associated with dysbiosis of the skin microbiome and the high susceptibility of these subjects to colonization and infections by pathogenic bacterial species such as *S. aureas*.

An alternative and promising approach is not to disrupt bacterial colonization, but rather to re-establish a healthy microbiome community on the skin. To do this a screen for naturally occurring, and sometimes rare commensal species on healthy human skin that express antimicrobial activity against skin pathogens was performed. A recent example is the discovery of commensal *staphylococcus* strains that produce lantibiotics that when applied to skin of patients with AD, demonstrated clinically improved symptoms and reductions of lesional *S. aureas* counts (Nakatsuji et al., 2017). Other studies have reported antimicrobial *staphylococcus* strains belonging to species of *S. lugdunensis* (Zipperer et al., 2016), *S. epidermidis* (Cogen et al., 2010) and *S. capitis* (O'Neill et al., 2020) isolated from different niches of the skin and nares. In contrast, very little is known regarding the antimicrobial activity of animal-derived staphylococci and their clinical potential against skin infection.

It was hypothesized that the screening of poorly characterized bacterial species from diverse body sites of healthy animals could be a promising strategy to discover new antimicrobial strains that are effective against zoonotic pathogens. *Staphylococcus felis* (*S. felis*) is a constituent of the microflora of cats and other domesticated animals. *Staphylococcus felis* is a Gram-positive, coagulase-negative member of the bacterial genus *Staphylococcus* consisting of clustered cocci. The disclosure demonstrates that certain common non-pathogenic staphylococci from the skin of animals can out-compete more pathogenic bacteria, and therefore be used as a therapeutic for the treatment of bacterial infections in animals.

Following the high-throughput antimicrobial screening of a collection of diverse animal-derived staphylococci, *S. felis* C4 was identified, which secretes antimicrobials targeting MRSP and other clinically relevant, drug-resistant gram-positive pathogens. *S. felis* remains poorly characterized in the literature, but is the most frequent species of staphylococci isolated from cats and is susceptible to most antimicrobials (K. Worthing et al., 2018). In the experiments described herein, *S. felis* isolates were screened and showed antimicrobial activity in liquid and agar co-culture. Importantly, topical application of the live *S. felis* C4 organism outcompeted MRSP colonization in vivo, likely by the active secretion of its antimicrobials on the skin surface. Indeed, topical application of the sterile extract was similarly effective in reducing CFU counts on mouse skin. Injection of the extract during *S. pseudintermedius* skin infection was also effective in significantly reducing the size of necrotic lesions. These positive in vivo findings demonstrate the utilization of commensal bacteria as biotherapeutic products to treat skin diseases.

The disclosure identifies *S. felis* C4 as a potent antimicrobial isolate from feline skin that inhibited the growth of MRSP in vitro and in vivo. *S. felis* C4 produced several α-helical amphipathic peptides (AMPs) that demonstrated antimicrobial and anti-inflammatory activity. This discovery represents a potential new bacteriotherapeutic for human and canine skin diseases associated with *S. pseudintermedius* colonization and infection.

This disclosure provides compositions and formulations for disinfecting surfaces or treating infections while not posing the safety risks of non-specific antibiotics or antimicrobial therapies. Further the disclosure provides for probiotic approaches wherein subjects may be provided with live or attenuated strains of *S. felis* including strain *S. felis* C4 which can produce antimicrobial compounds in situ while simultaneously restoring the characteristics of a healthy cutaneous flora.

Through the methods of the disclosure an isolate from feline skin that secreted small peptides having antimicrobial activity was isolated. The antimicrobial agents were easily extractable by established biochemical methods to obtain an antimicrobial extract preparation. The application compositions comprising the probiotic bacteria or extracts thereof onto infected mouse skin greatly reduced MRSP infection and colonization. These results highlight the clinical potential for transplantation of antimicrobial commensals to treat skin infections that are recalcitrant to classic antibiotic treatment.

Several phenol soluble modulins (PSMs) such as PSMβ peptides were identified by mass spectroscopy, that were highly enriched in an antimicrobial HPLC fraction from *S. felis* C4 supernatant. Their activity against the growth of MRSP was validated using synthetic versions of the peptides. Although individually they demonstrated some antimicrobial activity they exhibited less potency than the extract as a whole. As such, due to the partially purified nature of the extract, the contribution of other antimicrobials products cannot be ruled out. This could include the AMP PSMα which is known to co-elute with PSMβ by HPLC. Nevertheless, both fluorescence and electron microscopy of bacteria exposed to the extract showed drastic perturbations of the bacterial cell membrane and cell wall thickening, which is consistent with the membrane-targeting actions of amphipathic AMPs. The concomitant accumulation of bacterial ROS and decrease in ATP production are also consistent with bacterial membrane disruption and increased permeability.

In addition to their protection against pathogen colonization, skin commensals play important roles in promoting skin health and immune homeostasis. Although PSMs are common amongst staphylococci, pathogenic *S. aureas* exhibits a preference for PSMα production over PSMβ. In contrast, commensal staphylococci production of PSMβ is prioritized over the more toxic PSMα and PSMγ versions, a feature suspected to be an evolutionary adaptation to stably colonize skin. Naturally, *S. felis* C4 PSMβ and extract treatment of NHEKs yielded minimal evidence of cytotoxicity, whereas PSMα and PSMγ induced extensive cytotoxicity. These smaller PSMs are well characterized toxins that trigger pro-inflammatory responses. Whereas the larger PSMβ reportedly does not elicit pro-inflammatory activity in vitro—a finding that was supported by the data, little is known regarding other potential host responses to PSMβ exposure. It was speculated whether PSMβ might exhibit anti-inflammatory activities, and in the present context that activity would be therapeutically beneficial. Indeed, when both NHEKs and THP-1 macrophages were treated with *S. felis* PSMs or extract in the presence of TLR agonists, cytokine induction was reduced but most evidently by PSMβ2. RNA-Seq analysis of NHEKs revealed global suppression of inflammatory pathways typically activated by TLR3, in the presence of PSMβ2. Treatment of NHEKs with PSMβ2 alone showed the downregulation of genes associated with IL-1 and bacterial infection, suggesting that PSMβ promotes tolerance to commensal microbes.

The disclosure provides methods and compositions useful for reducing inflammation in skin or mucosal tissue comprising administering or contacting the skin or mucosal tissue with (i) PSMβ2, (ii) extracts of *S. felis* C4 comprising PSMβ2; and/or (iii) a probiotic composition comprising an *S. felis* C4 that produces PSMβ2. Accordingly, the disclosure shows that *S. felis* C4 bacterium is an attractive biotherapeutic candidate for skin disease that could benefit patients due to established low cytotoxicity and its broad-spectrum antimicrobial activity and anti-inflammatory activity.

The disclosure also demonstrates the killing of pathogenic bacteria from humans (e.g., *Staphylococcus aureus*) by bacteria from animals. The data presented herein shows killing of a human pathogen by an animal bacterial derived composition. More specifically the disclosure shows the killing of the human and animal pathogens, *S. aureas* and *S. pseudintermedius*, by a non-pathogenic bacteria from animals (e.g., *S. felis* isolate C4). This was tested by growing a broth culture of *Staphylococcus felis* from a cat and plating this onto a lawn of *Staphylococcus aureus*. The *S. aureas* was inhibited by the *S. felis* isolate. Numerous bacterial isolates were similarly screened for antibacterial activity. The data show that out of the various isolates tested *S. felis* demonstrated the most potent antibacterial activity.

The disclosure provides for compositions, extracts and preparations of, or from, *S. felis* C4 that can be used as a probiotic strain of skin bacteria or composition that can be transplanted onto or contacted with diseased skin of various animals including, but not limited to, dogs, cats and dairy cows to outcompete and kill pathogenic bacteria that are causing infections such as bacterial pyoderma and mastitis. Killing of pathogenic bacteria in diseased skin will result in resolution of the infection. Moreover, the disclosure demonstrates that extracts and recombination preparations of expressed peptides from *S. felis* can be used to treat such diseases. The purified antimicrobial peptide from *S. felis* can be synthesized through information gathered by the genome sequence and protein structural data. This synthesized protein may be used as a topical antimicrobial treatment of skin infections in, for example, dogs, cats and dairy cows. In this context, the disclosure provides polypeptide sequence obtained from *S. felis* that show antimicrobial activity. These sequences can be used to generate and clone coding sequence for the polypeptides as well as provide sequence for peptide synthesis.

The disclosure also provides for antimicrobial peptides (AMPs) and extracts from culture supernatant of a clinical isolate of *S. felis* (e.g., *S. felis* C4). These extracts and AMPs have bactericidal activity against *Staphylococcus aureus* (*S. aureas*), as well as *S. pseudintermedius* but do not inhibit the growth of commensal bacteria on the skin/coat of such animals. Therefore, the disclosure provides antimicrobials or extracts comprising such antimicrobials with potent but selective activity against pathogens, and high safety profile as they are found normally in the skin/coat microbiome of healthy mammals, as well as probiotic approaches to treating these conditions.

The disclosure also provides peptides that are conservative variations of those peptides as exemplified herein. The term "conservative variation" as used herein denotes a polypeptide in which at least one amino acid is replaced by another, biologically, chemically, or structurally similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. Structurally conservative variations include the substitution of alanine for serine (and vice versa), isoleucine for threonine (and vice versa), arginine for lysine (and vice versa), and the replacement of any of tyrosine, phenylalanine, tryptophan, and histidine for any other member of that group. The term "conservative variation" also encompasses a peptide having a substituted amino acid in place of an unsubstituted parent amino acid; typically, antibodies raised to the substituted polypeptide also specifically bind the unsubstituted polypeptide.

The amino acids of a peptide, variant or peptidomimetic of the disclosure are selected from the twenty naturally occurring amino acids, including, unless stated otherwise, L-amino acids and D-amino acids. The use of D-amino acids are particularly useful for increasing the life of a protein or peptide. Polypeptides incorporating D-amino acids are resistant to proteolytic digestion. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. Other examples of amino acids and amino acids analogs are listed in Gross and Meienhofer, The Peptides: Analysis, Synthesis, Biology, Academic Press, Inc., New York (1983). An amino acid also can be an amino acid mimetic, which is a structure that exhibits substantially the same spatial arrangement of functional groups as an amino acid but does not necessarily have both the "-amino" and "-carboxyl" groups characteristic of an amino acid.

Polypeptides and peptides of the disclosure can be synthesized by commonly used methods such as those that include t-BOC or FMOC protection of alpha-amino groups. Both methods involve stepwise synthesis in which a single amino acid is added at each step starting from the C terminus of the polypeptide or peptide (See, Coligan, et al., Current Protocols in Immunology, Wiley Interscience, 1991, Unit 9). Polypeptide and peptides of the disclosure can also be synthesized by the well-known solid phase peptide synthesis methods such as those described by Merrifield, J. Am. Chem. Soc., 85:2149, 1962) and Stewart and Young, Solid Phase Peptides Synthesis, Freeman, San Francisco, 1969, pp. 27 62). If desired, the peptides can be quantitated by the solid phase Edman degradation.

The disclosure also includes isolated polynucleotides (e.g., DNA, cDNA, or RNA) encoding the polypeptide and peptides of the disclosure. Included are polynucleotides that encode analogs, mutants, conservative variations, and variants of the polypeptides and peptides described herein. DNA encoding the peptides, derivatives of variants thereof of the disclosure can be inserted into an "expression vector." The term "expression vector" refers to a genetic construct such as a plasmid, virus or other vehicle known in the art that can be engineered to contain a polynucleotide encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide of the disclosure can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

The disclosure also provides a method for inhibiting the growth of a bacterium including, but not limited to *S. aureas* and *S. pseudintermidius*, by contacting the bacterium with an inhibiting effective amount of a peptide or *S. felis* extract or probiotic composition comprising an *S. felis* of the disclosure. The term "contacting" refers to exposing the bacterium to the peptide or *S. felis* extract or *S. felis* composition so that the peptide, extract or composition can inhibit, kill, or lyse bacteria. The disclosure also provides a method for inhibiting skin disease or disorder and/or bacterial infection comprising placing on or within a subject a composition comprising bacteria, extract or peptides of the disclosure such that the growth of the pathogen or undesirable microbe is inhibited or prevented. Contacting of an organism with a peptide or *S. felis* extract or *S. felis* of the disclosure can occur in vitro, for example, by adding the peptide to a bacterial culture to test for susceptibility of the bacteria to the peptide, extract or composition, or contacting a bacterially contaminated surface with the peptide or *S. felis* extract or *S. felis* composition. Alternatively, contacting can occur in vivo, for example by administering or contacting a subject with a peptide, extract or *S. felis* composition afflicted with a bacterial infection or susceptible to infection. Further, contacting can occur by exposing the bacterium to a probiotic formulation comprising bacterial strains that produce the peptide, or other peptide or non-peptide inhibitors of bacterial growth. In vivo contacting includes both parenteral as well as topical. "Inhibiting" or "inhibiting effective amount" refers to the amount of a probiotic composition, peptide or *S. felis* extract that is sufficient to cause, for example, a bacteriostatic or bactericidal effect. Bacteria that can be affected by the peptides of the disclosure include both gram-negative and gram-positive bacteria. For example, bacteria that can be affected include *Staphylococcus aureus, Staphylococcus pseudintermedius, Streptococcus pyogenes* (group A), *Streptococcus* sp. (*viridans* group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and *Branhamella catarrhalis*; Gram-positive bacilli such as *Bacillus anthracis, Bacillus subtilis*, P. acne *Corynebacterium diphtheriae* and *Corynebacterium* species which are diptheroids (aerobic and anerobic), *Listeria monocytogenes, Clostridium tetani, Clostridium difficile, Escherichia coli, Enterobacter species, Proteus* mirablis and other sp., *Pseudomonas aeruginosa, Klebsiella pneumoniae, Salmonella, Shigella, Serratia* sp., and *Campylobacter jejuni*. Infection with one or more of these bacteria can result in diseases such as pyoderma, mastitis, bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, blood born infections, fascitis, bronchitis, and a variety of abscesses, nosocomial infections, and opportunistic infections. Fungal organisms may also be affected by the probiotic compositions, peptides and *S. felis* extracts of the disclosure and include dermatophytes (e.g., *Microsporum canis* and other *Microsporum* sp.; and *Trichophyton* sp. such as *T. rubrum*, and *T. mentagrophytes*), yeasts (e.g., *Candida albicans*, C. *Tropicalis*, or other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus,*

*Aspergillus nidulans*, and other *Aspergillus* sp., *Zygomycetes* (e.g., *Rhizopus, Mucor*), *Paracoccidioides brasiliensis, Blastomyces dermatitides, Histoplasma capsulatum, Coccidioides immitis*, and *Sporothrix schenckii*. The method for inhibiting the growth of bacteria can also include contacting the bacterium with the peptide or *S. felis* extracts in combination with one or more antibiotics.

A peptide(s) or *S. felis* extracts of the disclosure can be administered to any host, including a human or non-human animal, in an amount effective to inhibit growth of a bacterium or fungus. Thus, the peptides or *S. felis* extracts are useful as antimicrobial agents, antiviral agents, and/or antifungal agents. The bacterial strains that produce the peptides are useful as probiotic agents.

Any of a variety of art-known methods can be used to administer the peptide or *S. felis* extracts to a subject. For example, the peptide or *S. felis* extracts of the disclosure can be administered parenterally by injection or by gradual infusion over time. The peptide or *S. felis* extracts can be administered intravenously, intraperitoneally, intramuscularly, subcutaneously, intracavity, topically or transdermally. In another embodiment, a peptide or *S. felis* extracts of the disclosure may be formulated for topical administration (e.g., as a lotion, cream, spray, gel, oil suspension, or ointment). Examples of formulations in the market place include topical lotions, creams, soaps, wipes, powders, devices like gauze pads to cover wounds, and the like. It may be formulated into liposomes to reduce toxicity or increase bioavailability or stability. Other methods for delivery of the peptide or *S. felis* extracts include oral methods that entail encapsulation of the peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a peptide of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, chelating agents, inert gases and the like also can be included.

The disclosure provides a method for inhibiting a topical bacterial or fungal-associated disorder by contacting or administering a therapeutically effective amount of a peptide, *S. felis* extracts or skin-probiotic comprising an *S. felis* C4 or recombinant bacteria (e.g., attenuated bacteria) of the disclosure to a subject who has, or is at risk of having, such a disorder. The term "inhibiting" means preventing or ameliorating a sign or symptoms of a disorder (e.g., a rash, sore, and the like). Examples of disease signs that can be ameliorated include an increase in a subject's blood level of TNF, fever, hypotension, neutropenia, leukopenia, thrombocytopenia, disseminated intravascular coagulation, respiratory distress, shock, pustules and organ failure. Examples of subjects who can be treated in the disclosure include human or animal subjects at risk for, or those suffering from, a toxemia, such as endotoxemia resulting from a gram-negative bacterial infection, venom poisoning, or hepatic failure. Other examples include subjects having a dermatitis as well as those having skin infections such as pyoderma, mastitis and especially bovine mastits, or injuries subject to infection with gram-positive or gram-negative bacteria or a fungus. Examples of candidate patients include those suffering from infection by *E. coli*, Hemophilus influenza B, *Neisseria meningitides*, staphylococci, or pneumococci. Other patients include those suffering from gunshot wounds, renal or hepatic failure, trauma, burns, immunocompromising infections, hematopoietic neoplasias, multiple myeloma, Castleman's disease or cardiac myxoma. Those skilled in the art of medicine can readily employ conventional criteria to identify appropriate subjects for treatment in accordance with the disclosure.

The term "therapeutically effective amount" as used herein for treatment of a subject afflicted with a disease or disorder means an amount of peptide, extract or probiotic composition sufficient to ameliorate a sign or symptom of the disease or disorder. For example, a therapeutically effective amount can be measured as the amount sufficient to decrease a subject's symptoms of dermatitis or rash by measuring the frequency of severity of skin sores. Typically, the subject is treated with an amount of peptide, extract or probiotic composition sufficient to reduce a symptom of a disease or disorder by at least 50%, 90% or 100%. Generally, the optimal dosage will depend upon the disorder and factors such as the weight of the patient, the type of bacterial or fungal infection, the weight, sex, and degree of symptoms. Nonetheless, suitable dosages can readily be determined by one skilled in the art. Typically, a suitable dosage is 0.5 to 40 mg peptide/kg body weight, e.g., 1 to 8 mg peptide/kg body weight.

If desired, a suitable therapy regime can combine administration of a peptide(s), extract or probiotic composition of the disclosure with one or more additional therapeutic agents (e.g., an inhibitor of TNF, an antibiotic, and the like). The peptide(s), other therapeutic agents, and/or antibiotic(s) can be administered, simultaneously, but may also be administered sequentially. Suitable antibiotics include aminoglycosides (e.g., gentamicin), beta-lactams (e.g., penicillins and cephalosporins), quinolones (e.g., ciprofloxacin), and novobiocin. Generally, the antibiotic is administered in a bactericidal amount. However, the peptide provides for a method of increasing antibiotic activity. Typically, the peptide and antibiotic are administered within 48 hours of each other (e.g., 2 to 8 hours, or may be administered simultaneously). A "bactericidal amount" is an amount sufficient to achieve a bacteria-killing blood concentration in the subject receiving the treatment. In accordance with its conventional definition, an "antibiotic," as used herein, is a chemical substance that, in dilute solutions, inhibits the growth of, or kills microorganisms. Also encompassed by this term are synthetic antibiotics (e.g., analogs) known in the art.

The probiotics, peptides or *S. felis* extracts of the disclosure are also useful in promoting wound repair and tissue regeneration. Matrix metalloproteinases (MMPS) are inflammatory enzymes that degrade proteins in various tissues. Recent scientific research has shown elevated levels of proteases (e.g., MMPs) in chronic wound exudate, the fluid that bathes the wound bed. These excess proteases cause degradation of important extracellular matrix proteins and inactivation of vital growth factors that are essential in the wound healing process. This may contribute to a suboptimal healing environment resulting in delayed wound healing.

Compositions provided herein can be used concurrently with other antibacterial agents including sulfa drugs such as sulfamethizole, sulfisoxazole, sulfamonomethoxine, sulfamethizole, salazosulfapyridine, silver sulfadiazine and the like; quinoline antibacterial agents such as nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like; antiphthisics such as isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like; antiacidfast bacterium drugs such as diaphenylsulfone, rifampicin and the like; antiviral drugs such as idoxuridine, acyclovir, vidarabine, ganciclovir and the like; anti-HIV agents such as zidovudine, didanosine, zalcitabine, indinavir sulfate ethanolate, ritonavir and the like; antispirocheteles; antibiotics such as tetracycline hydrochloride, ampicillin, piperacillin, gentamicin, dibekacin, kanendomycin, lividomycin, tobramycin, amikacin, fradiomycin, sisomycin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt thereof, griseofulvin, lankacidin-group and the like.

In humans, there are several classes of known antimicrobial peptides (AMPs) including α-defensins, β-defensins, and cathelicidins. Cathelicidins are found in several mammalian species. Production of cathelicidins is induced in response to epithelial wounding or infectious challenge, or suppressed by the virulence mechanisms of certain bacterial pathogens, e.g., *Shigella dysenteriae*. Cathelicidin expression is also differentially effected in certain chronic inflammatory disorders. In psoriasis, cathelicidin levels are elevated and secondary infection is rare, whereas in atopic dermatitis cathelicidin expression is deficient and bacterial or viral superinfection is common. Therapeutic benefits of cathelicidin have been demonstrated experimentally, including decreased bacterial colonization of skin wounds following topical administration and improved pulmonary bacterial clearance with cathelicidin overexpression through viral gene transfer. The peptides of the disclosure show a synergistic effect with cathelicidins. Thus, in some embodiments a formulation, composition and method comprise both a peptide or *S. felis* extracts and cathelicidin. In some embodiments, a topical formulation (e.g., a lotion, ointment or aerosol spray) can comprise both a cathelicidin and peptide (or derivatives thereof).

Cathelicidin proteins are composed of two distinct domains: an N-terminal "cathelin-like" or "prosequence" domain and the C-terminal domain of the mature AMP. The C-terminal domains of cathelicidins were among the earliest mammalian AMPs to show potent, rapid, and broad-spectrum killing activity. The term "cathelin-like" derives from the similarity of the N-terminal sequence with that of cathelin, a 12 kDa protein isolated from porcine neutrophils that shares similarity with the cystatin superfamily of cysteine protease inhibitors.

Cathelicidins are expressed in neutrophils and myeloid bone marrow cells and most epithelial sources, and were the first AMPs discovered in mammalian skin due to their presence in wound fluid. In the neutrophil, cathelicidins are synthesized as full-length precursor and targeted to the secondary granules where they are stored. Upon stimulation, the full-length cathelicidin protein is proteolytically processed to unleash the microbiocidal activity of the C-terminal peptide from the cathelin-like domain.

The C-terminal 37 amino acids of human cathelicidin (LL-37) has been characterized. LL-37 was originally referred to as FALL39, named for the first 4 N-terminal amino acids of this domain and the total number of residues (i.e., 39). LL-37 is a peptide predicted to contain an amphipathic alpha helix and lacks cysteine, making it different from all other previously isolated human peptide antibiotics of the defensin family, each of which contain 3 disulfide bridges.

The polypeptide comprising SEQ ID NO:9 has a number of distinct domains. For example, a signal domain comprising a sequence as set forth from about 1 to about 29-31 of SEQ ID NO:9 is present. The signal domain is typically cleaved following amino acid number 30 of SEQ ID NO:9, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 30 of SEQ ID NO:9. Another domain comprises the N-terminal domain, referred to as the cathelin-like domain. The cathelin-like domain comprises from about amino acid 29 (e.g., 29-31) to about amino acid 128 (e.g., 128-131) of SEQ ID NO:9. Yet another domain of SEQ ID NO:9 comprises the C-terminal domain referred to as LL-37. The LL-37 domain comprises from about amino acid 128 (e.g., 128-134) to amino acid 170 of SEQ ID NO:9. LL-37 comprises the amino acid sequence set forth in SEQ ID NO:9.

(SEQ ID NO: 8)

```
MKTQRNGHSLGRWSLVLLLLGLVMPLAIIAQVLSYKEAV

LRAIDGINQRSSDANLYRLLDLDPRPTMDGDPDTPKPVS

FTVKETVCPRTTQQSPEDCDFKKDGLVKRCMGTVTLNQA

RGSFDISCDKDNKREALLGDFFRKSKEKIGKEFKRIVQR

IDDELRNLVPRTES
```

The mechanisms by which cationic human antimicrobial peptides kill bacteria and fungi are generally through binding of the peptide to the microbial cell membrane, after which the membrane's proton gradient and integrity are lost.

Vitamin D3 (or its analogs) with (and in some embodiments in combination with a cathelicidin) can be administered systemically to treat systemic infections, in particular pneumonia, sepsis and TB. It may also be applied topically to treat infectious skin disorders. It may be used in combination therapy with antibiotics or to treat immunocompromised patients such as HIV positive individuals. In combination with immune stimulating approaches, it may therapeutically address cancer.

The compositions and methods of the disclosure may also comprise treating disorders of skin/coat dysbiosis by administration of an antimicrobial peptide, extract or an organism secreting an antimicrobial compound, or administration of a probiotic composition comprising organisms that support skin health. In some embodiments, the composition includes a second active agent (e.g., an antibiotic, vitamin D3, cathelicidin etc.).

In some embodiments, the compositions described herein comprise a probiotic organism. In further embodiments, the probiotic organism is a bacterium. In further embodiments, the bacterium comprises a component of the normal skin flora. In further embodiments, the bacterium comprises a strain of *Staphylococcus felis*. In other embodiments, the probiotic organism comprises a mixture of strains. In some embodiments, the mixture of strains comprises multiple strains of *S. felis*. In other embodiments, the mixture of strains comprises one or more strains of *S. felis* and one or more strains of *S. epidermidis*. In some embodiments, the composition comprises one or more strains in addition to *S. felis*, including *S. hominis* and/or *S. epidermidis*. In some further embodiments, the additional strain or strains comprise one or more strains from the genus *Staphylococcus, Lactobacillus* or *Lactococcus*. For example, specific formulations may comprise *Staphylococcus felis*, in particular, *Staphylococcus felis* strain C4. The formulation can include other probiotic or commensal bacterial species including *Staphylococcus hominis* strain C2, *Staphylococcus hominis* strain AMT2, *Staphylococcus hominis* strain AMT3, *Staphylococcus hominis* strain AMT4-C2, *Staphylococcus hominis* strain AMT4-G1, *Staphylococcus hominis* strain AMT4-D12, *Staphylococcus epidermidis* strain AMT1, *Staphylococcus epidermidis* strain SE-All, *Staphylococcus epidermidis* strain AMT5-05, and/or *Staphylococcus epidermidis* strain AMT5-G6. Such formulations typically comprise sufficient quantities of bacterial cells as to provide a final density of $10^3$-$10^6$ CFU/cm$^2$ when applied to the skin of a subject. Such formulations may comprise concentrations of from about $10^4$ to about $10^7$ CFU/g, or alternatively, from 10 to about $10^5$ CFU/g, or alternatively, from about $10^5$ to about $10^9$ CFU/g. Such formulations may comprise multiple strains of *S. felis*, and may further comprise *Lactococcus lactis, Lactobacillus plantarum, Lactobacillus rhamnosus, Lactobacillus acidophilus*, and/or other such species or strains as are known in the art to form a part of the normal healthy cutaneous or mucosal flora. In some embodiments, *S. felis* strains as described above comprise 100% of the bacterial cells in a formulation. In some further embodiments, *S. felis* comprises 90-100%, 85-95%, 70-80%, 75-85%, 60-70%, 65-75%, 50-60%, 55-65%, 40-50%, 45-55%, 30-40%, 35-45%, 20-30%, 25-35%, 10-20%, 15-20%, 1-10%, 5-15%, or less than 1% of the bacterial cells in a given formulation, wherein the remainder of the colony forming units are provided by other commensal bacterial species such as *S. epidermidis, Lactococcus lactis, Lactobacillus plantarum, Lactobacillus rhamnosus, Lactobacillus acidophilus*, and/or other such strains as are known in the art to form a part of the normal healthy cutaneous or mucosal flora. In some embodiments, *S. felis* strains as described above comprise 100% of the bacterial cells in a formulation.

As used herein, an autologous transplant refers to the transplantation of bacterial strains from one site to another on the same subject or to the same site, regardless of whether the strains are cultured prior to administration or not. In some embodiments, the bacterial strains obtained from the subject are expanded in culture and then transplanted back to the subject.

As used herein, an allogeneic transplant refers to the transplantation of bacterial strains from one subject to another subject, or to the administration to a subject of a composition comprising bacterial strains that were not collected from upon or within their own body.

Such collection can be carried out by swabbing, scraping, wiping, or cutting and removing tissue on which resides one of the bacterial strains as described herein; optionally growing and isolating single colonies from agar plates or otherwise using methods known in the art; optionally growing expanded cultures of the isolated bacteria or crude swabs, wipes, scrapes, tissue, or other isolate in liquid or solid culture according to methods known in the art; optionally harvesting bacteria from said expanded culture by centrifugation, filtration, gravity settling, scraping, or by other means known in the art; formulating the bacteria or the crude isolate with a thickener, carrier, or excipient; and contacting the subject in an area determined to be in need of the transplant, with said formulation.

As used herein, a prebiotic compound comprises a polysaccharide, hydrolysate, salt, herbal extract, or any other compound sufficient to foster the growth of an associated probiotic strain when used in combination with that strain, such as yeast hydrolysate in concentrations of less than about 40% (w/w), microcrystalline cellulose in concentrations of less than about 10% (w/w), and/or sucrose in concentrations of less than about 10% (w/w). Other examples of prebiotics that may be adapted for use with cutaneous bacteria include inulin, glucooligosaccharides, isomaltooligosaccharides, lactosucrose, polydextrose, soybean oligosaccharides, and xylooligosaccharides, and those disclosed in Gibson, G. R. and Roberfroid, M, (Eds.) *Handbook of Prebiotics*, CRC press (2008); Roberfroid, M., J. Nutr. 137(3):830S-837 (2007) and Slavin, J. Nutrients 5(4): 1417-1435 (2013), each of which is incorporated herein by reference in its entirety.

In some embodiments the method comprises contacting a subject with a probiotic and/or prebiotic composition as described herein. In some embodiments, such contact comprises an autologous transplant. In some embodiments such contact comprises an allogeneic transplant, wherein elements of the cutaneous or mucosal flora are transplanted to a first subject in need thereof from a second subject (the donor). For example, in some embodiments, bacterial strains as disclosed above are identified and isolated from a second subject, amplified in an appropriate culture medium under such conditions as are known in the art to be conducive to bacterial growth, followed by harvest of the bacterial cells, mixing of the harvested cells at a predetermined concentration according to the disclosure with a predetermined formulation, wherein the formulation comprises an *S. felis* strain (e.g., *S. felis* C4) and application of the mixture to the affected area of the first subject. In some embodiments such composition comprises a standardized formulation, such as a formulation in which the concentrations of ingredients are fixed and are not varied from subject to subject. In some embodiments, the formulation is developed individually for each subject, based on criteria including but not limited to: the composition of the subject's own cutaneous or mucosal flora; the subject's disease state and treatment history; the nature and severity of the subject's condition; the nature and severity of concurrent cutaneous or mucosal infections; the presence of other antimicrobial compounds including systemic antibiotics within the subject's body; and other criteria such as are known to or would readily be apparent to those of skill in the art.

In some embodiments, the composition comprises a cream, ointment, oil suspension or unguent wherein the probiotic bacteria as described above are incorporated within a moisturizer or emulsion such as those described below and in Nakatsuji, T. et al. (2016), Nature Medicine Submitted Manuscript No. NMED-A78395A, submitted Mar. 29, 2016. In some embodiments, the composition comprises a patch or poultice wherein the bacteria are combined with a suitable excipient and are incorporated within a fabric, gel matrix, or polymer sheet. Suitable excipients and carriers for topical administration are known in the art and include thickeners, emulsifiers, fatty acids, polysaccharides, polyols, and polymers and copolymers, including, without limitation, alginate, microcrystalline cellulose, polylactic acid, polylactic-co-glycolic acid, petrolatum, and numerous others known in the art.

In some embodiments, the composition comprises a bacterial culture medium, a conditioned bacterial culture medium, and/or a bacterial culture comprising, e.g., *S. felis* C4. In some embodiments, the composition comprises a filtrate or supernatant of a bacterial culture medium. In some embodiments, the composition comprises a lyophilized culture medium. In some embodiments, the composition comprises a lyophilized conditioned culture medium produced from a filtrate or supernatant of a bacterial culture medium.

In some embodiments, the method as described herein comprises supporting the health of the skin of a subject. In further embodiments, the method comprises providing a treatment for skin dysbiosis and disorders derived therefrom. In some embodiments the method comprises providing a treatment for bacterial infection of the skin. In some embodiments, the treatment comprises the steps of: identifying a subject with skin dysbiosis, bacterial infection, pyoderma, mastitis, burn or other wound, atopic dermatitis, psoriasis, or other chronic skin condition; and administering to the site of the condition in need of treatment a probiotic composition, peptide or *S. felis* extracts as disclosed herein. Determination of the appropriate mode of administration of a given formulation (ointment, gel, patch, etc.) can be done by one of ordinary skill in the art of treating skin infections. In some further embodiments, the probiotic compositions are re-applied at regularly timed intervals. In some embodiments, the probiotic composition, peptide or *S. felis* extracts are reapplied every three days. In some embodiments, the probiotic composition, peptide or *S. felis* extracts are reapplied every two days. In some embodiments, the probiotic compositions are reapplied every two days. In some embodiments, the probiotic composition, peptide or *S. felis* extracts are reapplied daily. In some embodiments, the probiotic composition, peptide or *S. felis* extracts are reapplied more than once per day. In some embodiments, the probiotic composition, peptide or *S. felis* extracts are reapplied weekly. In some embodiments, the probiotic compositions, peptide or *S. felis* extracts are only applied a single time.

The following examples are intended to illustrate but not limit the disclosure. While they are typical of those that might be used, other procedures known to those skilled in the art may alternatively be used.

EXAMPLES

Example 1

Sample collection. Purified cultures of staphylococci from animals (n=42) were used as competitor isolates to determine if they killed human and animal staphylococcal pathogens. Samples came from two collections: the first collection consisted of clinical isolates of skin and soft tissue infection from Australian dogs and cats, and a second collection of staphylococci isolated from the nose, mouth and perineum of healthy dogs and cats in rural Australia. Samples included *S. pseudintermedius* isolated from dogs (sites of infection, n=7; carriage sites, n=8), *S. felis* from cats (sites of infection, n=8; carriage sites, n=8) and assorted species of coagulase negative staphylococci isolated from carriage sites from healthy dogs (n=16). Five isolates were used as pathogens: *S. aureas* 113, two methicillin-resistant *S. pseudintermedius* strains (ST71 and ST496) and two methicillin-susceptible *S. pseudintermedius* strains (ST540 and ST538). The *S. pseudintermedius* isolates were all isolated from sites of infection in dogs, the *S. aureas* strain was a laboratory derived strain.

Radial diffusion assay for killing of *Staphylococcus aureus* and *Staphylococcus* pseudintermedius by animal staphylococci. To test for inhibitory action of the competitor isolates against pathogenic *S. aureas* and *S. pseudintermedius*, competitor broth cultures were inoculated onto 1% tryptone soy agar plates containing *S. aureas* or *S. pseudintermedius* as follows. 'Pathogen' agar plates were prepared by inoculating 2 μL 24 hour broth culture (approximately $1\times10^7$ CFU/ml) into 12 ml 1% tryptone soy agar. The agar was then air-dried then a 5 μL droplet of each competitor broth culture was placed onto the *S. aureas* or *S. pseudintermedius* agar. Known antimicrobial peptide producer, *S. hominis* A9, was used as a positive control. Tryptone soy broth without competitor bacteria was used as a negative control. Plates were incubated overnight at 30° C. for *S. aureas* and 37° C. for *S. pseudintermedius*. The plates were then examined for inhibitory activity, indicated by a zone of clear agar (absence of *S. aureas* or *S. pseudintermedius* growth) around the droplet of the competitor isolate.

Liquid assay for killing of pathogens by cell-free supernatant of animal staphylococci broth culture. To determine if pathogen killing was mediated by an extracellular product produced by competitor isolates, cell-free supernatant was prepared from the isolates that showed inhibitory activity on radial diffusion assay. Overnight tryptone soy broth cultures of competitor isolates were centrifuged at 4000 rpm at 4° C. for 15 min, then the supernatant was filtered using a 0.2 μm micropore filter 96-well plate by instilling 200μl into the plate and then centrifuging at 4000 rpm for 3 min. 10 μL of filtered supernatant ('conditioned media') was then added to 90 μL of $1\times10^5$ CFU/mL *S. aureas* broth culture, resulting in a final concentration of 10% conditioned media. 90 μL of pathogen culture was also inoculated into 10 μL tryptone soy broth to be used as the negative control. Pathogen/conditioned media cultures were then incubated in a 96-well plate in a shaking incubator at 37° C. overnight. Pathogen death was determined by measuring culture turbidity (OD600) after 24 hr incubation. The OD600 of pathogen growth in conditioned media was compared to that in tryptone soy broth to determine the extent of pathogen killing.

Isolates that demonstrated more than 50% reduction in *S. aureas* growth relative to the TSB negative control underwent further purification, as follows.

Protein purification of isolates with inhibitory cell-free supernatant. Inhibitory isolates from the liquid killing assay were precipitated in 50% and 70% ammonium sulphate saturate. The precipitate was resuspended in sterile water then filtered with a 0.2 μm membrane. Inhibitory action of the precipitate was confirmed in a radial diffusion assay against *S. aureas* 113, as described above. Precipitates that were inhibitory then underwent HPLC purification using a CapCel Pak C8 column (5 μm, 300 Å, 4.6×250 mm) (Shiseido Co.) with a linear gradient of acetonitrile from 20% to 55% in 0·1% (v/v) TFA at 0.8 mL/min. Acetonitrile was removed from HPLC eluted fractions by lyophilization in a vacuum centrifuge. Lyophilized fractions were reconstituted in 25 mM phosphate buffered saline (pH=7.2) then the antimicrobial activity of each fraction was determined in a liquid culture killing assay against *S. aureas* 113. The antimicrobial fractions from three HPLC runs were pooled together in a further purification step, using the same C8 cartridge but with a linear gradient of acetonitrile from 20% to 50%. The purified antimicrobial products then underwent mass spectrometry as follows.

Influence of heat and proteinase-K digestion on AMP C4 activity. To test the influence of proteinase on the activity of AMP C4, the resuspended precipitate of *S. felis* C4 was incubated in 1 mg/mL proteinase-K at 37° C. for 1 hr then 95° C. for 10 min. The proteinase-K treated product then underwent radial diffusion assay against *S. aureas* 113, as described above, To determine whether the AMP was inactivated by heat, the reconstituted precipitate of cell-free conditioned media from *S. felis* C4 was incubated at 95° C. for 5 min, 15 min and 30 min then underwent radial diffusion assay as above.

Agr fluorescence assay. To assess whether quorum sensing by *S. aureas* was disrupted by competitor isolates, an agr fluorescence assay was undertaken. The YFP *S. aureas* strain has the agr gene fluorescently labelled-higher fluorescence indicates higher expression of the agr locus necessary for quorum sensing, lower fluorescence indicates lower agr expression. 10 ul YFP *S. aureas* was grown in 10% conditioned media from competitor isolates, as described above. The resulting broth cultures were then diluted 1:10 after 24-hour incubation. Fluorescence was measured using a fluorescent spectrometer. Agr fluorescence by *S. aureas* grown in conditioned media was compared to that of *S. aureas* grown in tryptone soy broth to determine the extent of agr inhibition by competitor conditioned media.

Figure 1B:
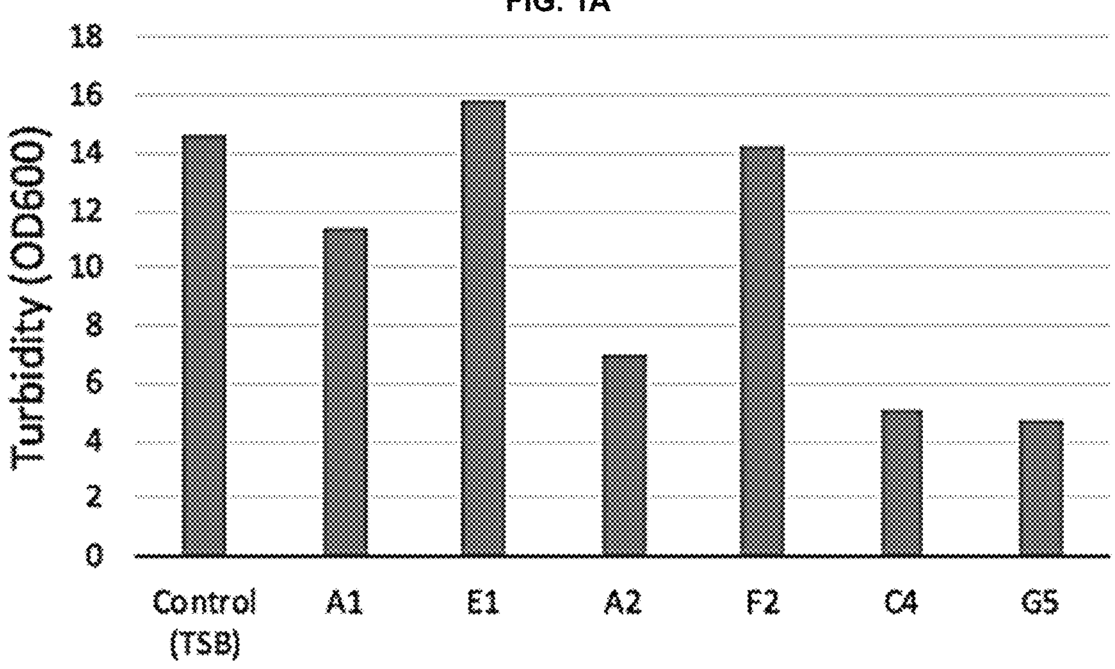
Figure 1C:
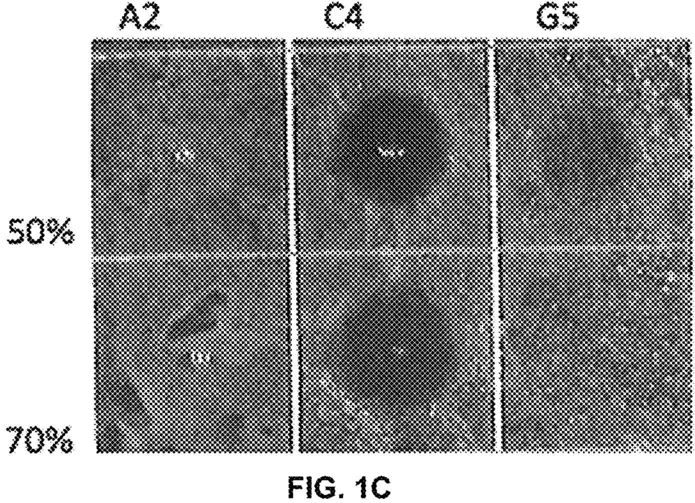
Figure 2:
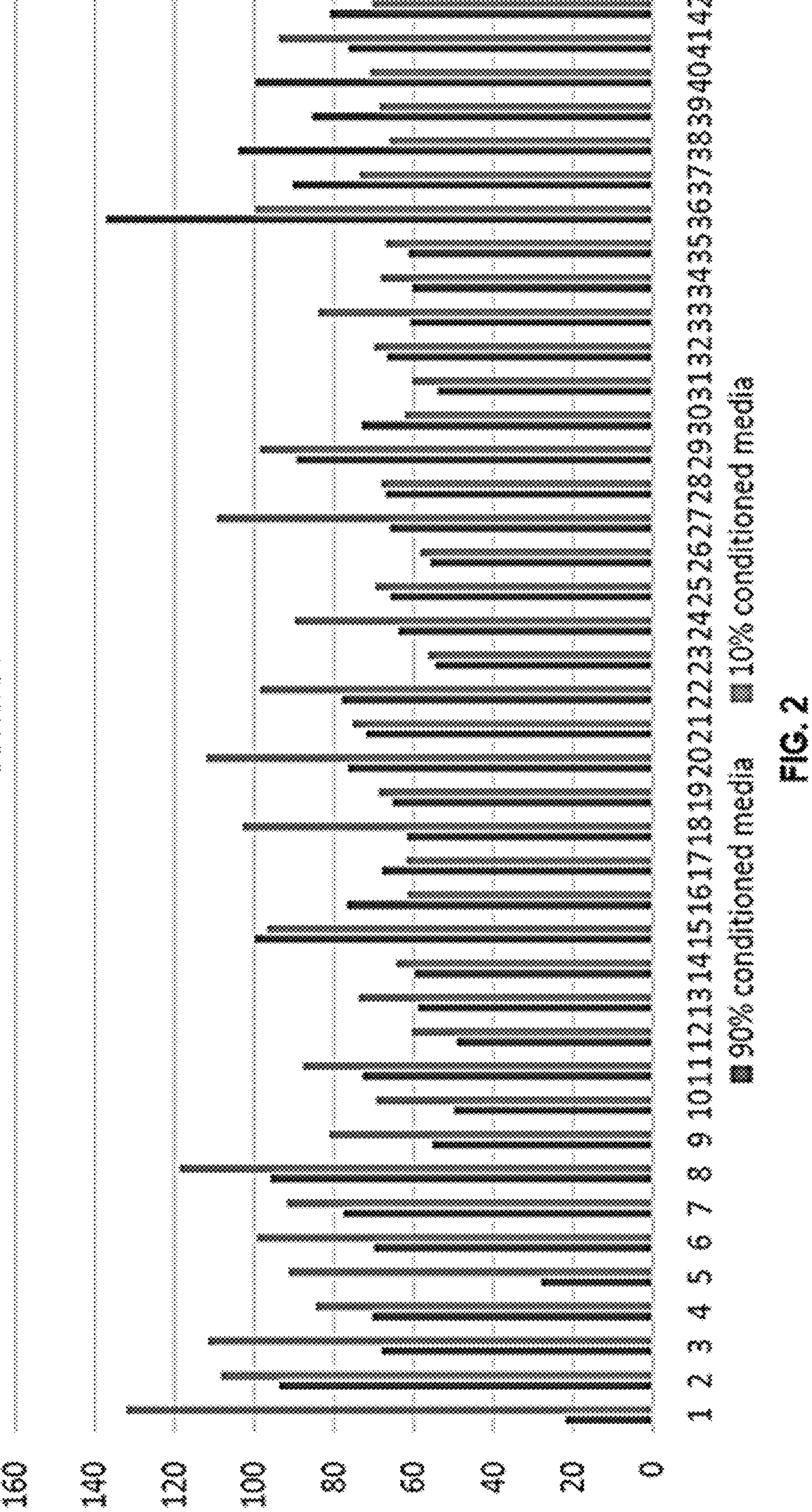
FIG. 2 shows conditioned media assay against *S. aureas* 113 and methicillin-resistant *S. pseudintermedius* ST71, using cell-free supernatant from 42 staphylococci isolated from animals.
Figure 2:
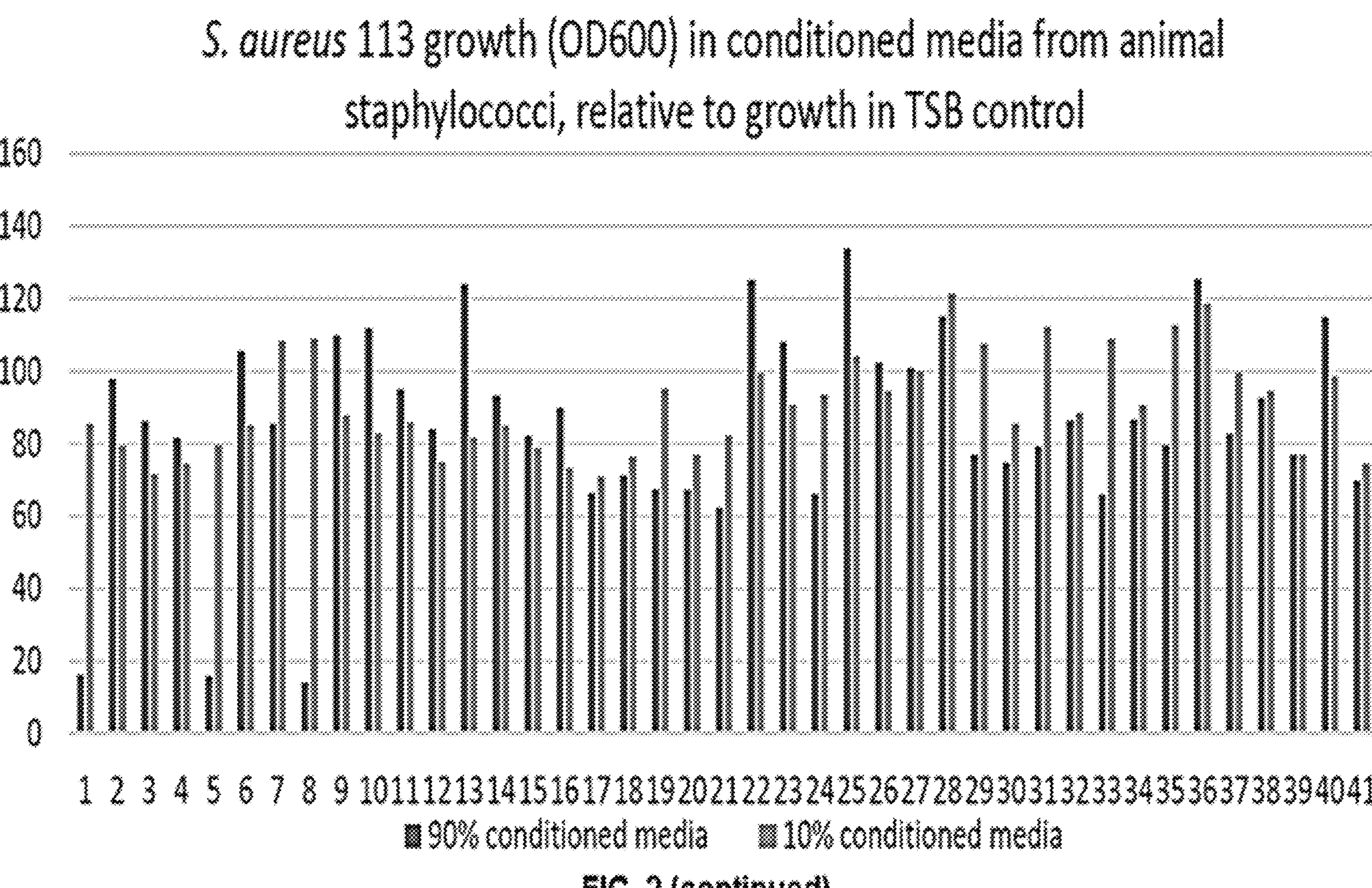

Inhibition of *S. aureas* and *S. pseudintermedius* by animal-derived staphylococci. In the radial diffusion assay, all pathogens were inhibited by *S. felis* isolate from a healthy cat (*S. felis* C4) and the positive control, *S. hominis* A9. Five other competitor isolates were variably inhibitory, with some *S. pseudintermedius* isolates being inhibited by *S. pseudintermedius* ST496 (A1 and E1) and *S. felis* F2 and G5 as shown in FIG. 1*a*. In the liquid killing assay, the cell-free conditioned media from *S. felis* isolates A2, C4 and G5 showed greater than 50% inhibition of *S. aureas* growth relative to growth in the TSB control (FIG. 1*b*). The conditioned media of these three isolates were precipitated at 50% and 70% ammonium sulphate saturation, but only C4 retained inhibitory activity after precipitation (FIG. 1*c*). The precipitate of C4 underwent further characterization as outlined below.

Characterization of an antimicrobial peptide from *S. felis* C4. Inhibitory activity of C4 was maintained after exposure to 95° C. for 30 min, indicating it was heat stable. Inhibitory activity in the radial diffusion assay was also maintained after treatment with proteinase-K, indicating it was resistant to digestion by this protease.

Purification of the antimicrobial peptide from *S. felis* C4. The cell-free conditioned media from C4 was precipitated in ammonium sulphate at 50% saturation. The resuspended precipitate underwent HPLC, where the active fraction eluted in 37% acetonitrile. This fraction underwent a second HPLC purification step before undergoing mass spectrometry to ascertain the identity structure of the protein.

Example 2

Bacterial Strains and Growth Conditions

The bacterial strains used in this study were all grown overnight, with the exception of *E. faecium* which was grown for 48 h, in Tryptic Soy Broth (TSB) (Oxoid) with shaking or on agar at 37° C. under static conditions.

Sample Collection

Animal-derived staphylococci samples came from two previously described collections: the first collection consisted of clinical isolates of skin and soft tissue infection from Australian dogs and cats (K. A. Worthing et al., 2018), and the second collection was comprised of staphylococci isolated from the nose, mouth and perineum of healthy dogs and cats in Australia (Ma et al., 2020). All samples had previously been identified by matrix assisted laser desorption ionization-time of flight mass spectrometry (MALDI-TOF), as previously described (K. Worthing et al., 2018), and the ST71 MRSP isolate had been characterized by whole genome sequencing (K. A. Worthing et al., 2018). Two human derived antimicrobial skin commensal isolates were used as positive controls: *S. hominis* A9 (Nakatsuji et al., 2017) and *S. capitis* E12 (O'Neill et al., 2020) and a non-antimicrobial *S. aureas* 113 isolate served as a negative control.

In Vitro Antimicrobial Screen

For the initial staphylococci screen, single clone-derived cultures of animal-derived staphylococci were used as competitor isolates against the growth of methicillin-resistant *S. pseudintermedius* ST71. Each pure culture, including positive and negative control strains, were first streaked onto 3% TSB agar plates and a single colony was transferred to 1 ml of TSB in a deep 96 well plate (Thermo). The CoNS plate was sealed with sterile Aeraseal film (Sigma, St. Louis, MO) and cultured at 37° C. overnight with shaking at 250 rpm. Bacterial growth was evaluated by measuring OD600 with only bacteria that grew to a density (OD600>6.0) used for subsequent analysis. To measure antimicrobial activity in the secreted supernatant, the animal-derived staphylococci supernatant from overnight cultures were harvested and centrifuged through several 96-well 0.2 μm sterile filter plates (Corning). Next, $1\times10^5$ CFU of *S. pseudintermedius* ST71 was inoculated into 150 μl of 100%, 50% or 25% sterile supernatant supplemented with fresh 3% TSB and grown on a plate shaker for 18 h at 30° C. To measure antimicrobial activity from the live agar co-culture assays, 20 μl of overnight *S. pseudintermedius* ST71 culture was first inoculated into 45° C. molten TSB and immobilized after pouring and cooling into square petri dishes with grids. Overnight cultures of animal-derived staphylococci were centrifuged to pellet the bacteria, washed 2× with PBS and resuspended in fresh TSB. The culture (10 μl) was inoculated onto a 13 mm grid of the *S. pseudintermedius* agar plates and cultured overnight at 30° C. The resulting zones of inhibition from antimicrobial isolates were imaged using the camera feature on an iPhone 12.

Extraction and purification of antimicrobials from bacterial supernatant

Supernatant from overnight cultures of selected human and animal-derived staphylococci were first sterilized by filtration through a 0.22-μm Millipore filter. Activity was precipitated by ammonium sulfate (75% saturation) for 1 h, under constant rotation followed by centrifugation at 4,000×g for 45 min and re-suspension of the pellet in $dH_2O$. To test stability, the precipitate was boiled at 95° C. for 30 minutes or stored in a sterile eppendorf tube at room temperate for 1 week. Antimicrobial activity was measured by radial diffusion assay. Sterile supernatant of *S. felis* strains were subject to n-Butanol extraction and purification as previously reported (Joo and Otto, 2014). Briefly, in each tube 10 ml of butanol was added to 30 ml of supernatant and incubated at 37° C. for 2 h under constant rotation. The tubes were then set aside for several mins until the butanol phase settled. After centrifugation at 2000×g for 5 min, the upper butanol phase was collected and lyophilized in a SpeedVac vacuum concentrator. The lyophilized extract was resuspended and concentrated to 10 mg/ml in DMSO. Protein concentration was determined by Pierce BCA protein Assay Kit.

Determination of Minimum Inhibitory Concentration (MIC)

MIC values were determined using a broth micro dilution method. Bacterial cells were grown to mid-late log phase, to an $OD_{600}$ nm value of roughly 1.0 for each bacterial strain and then normalized to $1\times10^7$ CFU/mL. The PSMβ peptides or butanol extracts were dissolved in DMSO to a stock concentration of 10 mg/ml. The stock concentrations of antibiotics that were water-soluble were prepared with $H_2O$ or 100% ethanol if water-insoluble. The $1\times10^7$ CFU/ml bacterial cultures (10 μl) were aliquoted into 96-well microtiter plates and mixed with 95 μL of media with or without 2-fold dilutions of the conditioned supernatant, PSMβ peptides, butanol extracts or antibiotics and incubated for 16-18 h at 30° C. with shaking at 250 rpm. Growth inhibition was determined by measuring the OD600 nm readings of each well using a microplate reader (SpectraMax iD3, Molecular Devices). The MIC of each bacterial strain was determined by the lowest peptide concentration that inhibited more than 80% bacterial growth.

Crystal Violet Staining for Biofilm Disruption

Overnight culture of *S. pseudintermedius* ST71 was diluted in fresh TSB to $1\times10^7$ CFU/ml by OD600 reading. A total of 100 μl of bacteria was transferred to a flat-bottom 96 well plate and incubated at 37° C. without shaking for 4 h to initiate biofilm formation. Next, the supernatants were removed by washing the plates three times with 200 μl of $dH_2O$. Subsequently, 150 μl of *S. felis* C4 supernatant, extract, or PSMβ2 peptide at various concentrations, or TSB negative control, was added to the biofilm for periods between 2-24 h. After incubation, the supernatant was gently removed and the biofilm was washed three times with $dH_2O$ followed by air drying. Next, 150 μl of 0.1% crystal violet (CV) solution was added to all wells containing biofilm. After 20 mins of incubation with CV dye, the excess CV was removed and each well was washed twice with $dH_2O$. Fixed CV dye was released from the biofilm by 70% ethanol, and absorbance was measured at 595 nm.

Bacterial Cytological Profiling (BCP).

Prior to BCP, MIC of all the antimicrobial compounds to be tested were generated first. MICs for *B. subtilis* PY79 were conducted in 96-well plates. Cultures were taken from glycerol stocks and plated on LB plates for 24 hr at 30° C. On the day of the experiment, single colonies were transferred into 3 mL liquid LB media and rolled until they reached early exponential phase ($OD_{600}$ 0.12-0.15). In 96-well plates, antibiotics were serially diluted down two-fold across the plate. One μl of cells was added to 100 μL of LB+ antibiotic. Plates were incubated for 24 hr in a 30° C. plate shaker. Plates were then read in plate reader using an $OD_{600}$ nm spectrophotometer at TO and T24. MIC was determined by the concentration of antibiotic at which the T24 $OD_{600}$ value was 10% or less than the control cell density. BCP was performed. Briefly, early exponential phase *B. subtilis* PY79 was incubated with 0.5×, 1×, or 5×MIC concentrations of antibiotics and rolled at 30° C. for 2 hr. Samples were taken at 30 m and 2 hr, and then dye mix was added to each for each strain. The dye mix contained 30 μg $mL^{-1}$ FM 4-64, 20 μg $mL^{-1}$ DAPI, and 2.5 μM Sytox Green in 1× Tbase. Six μL of cells were mixed with 1.5 μL of dye mix, and then 6 μL of that mixture was added to agarose pads (1% agarose, 20% LB). Cells were then imaged on an Applied Precision DV Elite optical sectioning microscope with a Photometrics Cool-SNAP-HQ2 camera, and images were deconvolved using SoftWoRx v5.5.1. Deconvolved images were then converted into TIFFs using Fiji, and then adjusted for clarity in Photoshop, producing the final images.

HPLC Purification and Peptide Synthesis

First step HPLC purification was carried out with 1 mg of *S. felis* C4 supernatant loaded onto a Capcell Pak® C8 column (5 mm, 300 Å °, 4.6 mm 250 mm) (Shiseido, Tokyo, Japan) using a linear acetonitrile gradient from 10% to 60% in 0.1% (v/v) trifluoroacetic acid at a flow rate of 1.0 ml/min. The resulting fractions were lyophilized, then resuspended in water, and antimicrobial activity assessed by liquid culture assay. Up to five sequential purifications were carried out with each antimicrobial fraction pooled together for the second HPLC purification. A linear gradient of acetonitrile from 25% to 60% was used for the second purification. PSMβ peptides were synthesized with N-terminal formulation to at least 95% purity by a commercial vendor (LifeTein LLC, Somerset, NJ).

Sequences of the peptides are as follows (SEQ ID NO in parenthetical):

```
PSMβ1:                                              (3)
Formyl-MSGLIDAIKTTVEAGLNGEWADMGLGI
AEIVAKGIEAISGFFG

PSMβ2:                                              (4)
Formyl-MSDLINAIKTTVEAGLNGEWTDMGFGI
ADIVAKGIDVILGFFG

PSMβ2:                                              (5)
Non-Formyl-MSDLINAIKTTVEAGLNGEWTDM
GFGIADIVAKGIDVILGFFG

PSMβ3:                                              (6)
Formyl-MADLINAIKTTVEAGLNGEWTDMGFGI
ADIVAKGIDVISGFFG

PSMγ:                                               (7)
Formyl-MAADIISTIGDLVKWIIDTVNKFKK

EF-HAND:                                            (8)
Non-Formyl-MSKLTRVIVTSIMTVGFLTATL
GLTAGNADAKLEGNGTLSQKQYQRLASQQF
```

Silver Stain and Acetone Precipitation of Antimicrobial Fractions

Twenty μg of protein from sources including the antimicrobial HPLC fractions, butanol extracts and crude supernatant were loaded onto a Novex 16% Tricine gel and subjected to SDS-PAGE. Silver staining and de-staining of the protein gels were performed according to the manufacturer's instructions (Thermo Pierce Silver Stain Kit). A previously published protocol for acetone extraction of AMPs from SDS gels was used (Burgess, 2009). Briefly, a sterile razor blade was used to excise gel slices according to protein size. The gel slices were cut into small pieces and immersed in $dH_2O$ for 4 h, with regular vortexing to elute proteins. The eluted protein was mixed with four volumes of ice-cold acetone for 1 h at −20° C. The samples were centrifuged at 16,000×g for 15 mins at 4° C. The supernatant was removed and lyophilized (acetone-soluble fraction) and the resulting pellet air dried briefly and resuspended in $dH_2O$ (acetone-insoluble fraction). The antimicrobial activity of both fractions was tested by radial diffusion agar assay against *S. pseudintermedius* ST71.

NHEK Culture

NHEKs (ThermoFisher) were cultured in EpiLife medium containing 60 μM $CaCl_2$) (ThermoFisher) supplemented with 1× human keratinocyte growth supplement (ThermoFisher) and 1× Antibiotic Antimycotic (Millipore Sigma) at 37° C., 5% CO 2. All experiments performed on NHEKs were between passages 3 and 5 with cells at 70-80% confluency. For synthetic PSMβ treatments, the peptides (10-1000 μg/ml) were added to the NHEKs for 4 hr or 24 hr in dimethyl sulfoxide (DMSO).

Immunoblot

NHEK cells were lysed in complete RIPA buffer supplemented with 1× protease and phosphatase inhibitor cocktail (Life Technologies, USA). The lysate was centrifuged at 4° C., at 13,000 rpm for 20 min and the total cytoplasmic supernatant fraction was kept at −80° C., until future use. The total protein amount was quantified for each treatment using the Pierce™ BCA Protein Assay Kit according to manufacturer's instructions. Ten μg of total protein was loaded onto a 4-20% Mini-PROTEAN TGX gel (Bio-Rad), then transferred to a polyvinylidene difluoride (PVDF) membrane and probed with the following primary antibodies: P-TBK1/NAK (D52C2), TBK1/NAK (D1B4), P-IRF-3 (S396), IRF-3 (D83B9), COX IV (3E11). IRDye conjugated anti-rabbit and anti-mouse secondary antibodies (IRDye800CW; Licor, USA) were used. The images were acquired on an Odyssey CLx Imaging System (Licor, USA).

Mass Spectrometry

Four fractions of interest (ranging from 10-20 μg/mL) were dried under vacuum and resuspended in 15 μL of 5% acetonitrile with 5% formic acid. Next, individual LC-MS experiments were conducted on 6 μL of each sample through 85 minutes of data acquisition on an Orbitrap Fusion (Thermo Fisher Scientific) mass spectrometer with an in-line Easy-nLC 1000 (Thermo Fisher Scientific). A home-pulled and packed 30 cm column was triple-packed with 0.5 cm, 0.5 cm and 30 cm of 5 μm C4, 3 μm C18, and 1.8 μm C18 respectively and heated to 60° C. for use as the analytical column. Peptides were first loaded at 500 bar which was followed by a chromatography gradient ranging from 6 to 25% acetonitrile over 70 minutes followed by a 5-minute gradient to 100% acetonitrile, which was held for 10 minutes. Electrospray ionization was performed by applying 2000V through a stainless-steel T-junction connecting the analytical column and Easy-nLC system. Each sample was followed by four washes starting with a gradient from 3 to 100% acetonitrile over 15 minutes with an additional 10 minutes at 100% acetonitrile. An m/z range of 375-1500 was scanned for peptides with charge states between 2-6. Centroided data was used for quantitation of peaks. Acquisition was run in a data-dependent positive ion mode. Raw spectra was searched in Proteome Discoverer Version 2.1 against 6-frame translated databases based of a uniprot reference database for *Staphylococcus felis* ATCC 49168 (Uniprot proteome UP000243559, accessed Jun. 26, 2019) as well as in-house sequencing of *S. felis* C4. Data were searched using the Sequest algorithm (Eng et al., 1994) using a reverse database approach to control peptide and protein false discoveries to 1% (Elias and Gygi, 2007). No enzyme was specified in the search and a minimum peptide length was set to 6 amino acids. Search parameters included a precursor mass tolerance of 50 ppm and fragment mass tolerance of 0.6 Da and variable oxidation for modifications.

Whole Genome Sequencing of *S. felis* C4

DNA was extracted from *S. felis* C4 using the UltraClean™ Microbial DNA Isolation Kit (MoBio) according to the manufacturer's instructions. The library was prepared using Nextera DNA Flex library preparation kit according to the manufacturer's instructions (Illumina, San Diego, CA). The library was diluted to 1.0 nM, then sequenced for 300 cycles using the Illumina NovaSeq system to generate 150 bp paired-end reads with 794× coverage that was reduced to 100× coverage for read mapping. Fastq files from *S. felis* C4 were trimmed using Trimmomatic (Bolger et al., 2014), then assembled using SPAdes Genome Assembler v.3.14.1. The *S. felis* C4 genome was annotated using the RAST tool kit via the Pathosystems Resource Integration Center (PATRIC) database (Wattam et al., 2014) and genes encoding PSMβ were identified by BLASTn and secondary metabolite biosynthesis gene clusters by anti-SMASH bacterial version.

ATP Determination

The intracellular ATP levels of *S. pseudintermedius* ST71 treated with *S. felis* C4 butanol extract were measured following the manufacturer's instructions (ReadiUse™ Rapid Luminometric ATP Assay Kit). Briefly, an overnight *S. pseudintermedius* ST71 culture was sub-cultured to an OD of 0.5 at 37° C. The bacteria were pelleted, washed with fresh TSB and incubated with various concentrations (0-320 μg/ml) of *S. felis* C4 butanol extract for 1 h. The bacterial cultures were centrifuged at 10,000×g for 5 min at 4° C. The bacterial pellet was lysed by lysozyme and centrifuged. The bacterial supernatant was mixed with an equal volume of detecting solution in a 96 well plate and incubated at room temperature for 20 min. ATP luminescence was read using a SpectraMax iD3 (Molecular Devices).

Reactive Oxygen Species (ROS) Measurement

The levels of reactive oxygen species (ROS) in *S. pseudintermedius* ST71 that was treated with *S. felis* C4 butanol extract were measured with 2',7'-dichlorofluorescein diacetate (DCFDA) following the manufacturer's instructions (DCFDA/H2DCFDA Abcam cellular ROS assay kit). Briefly, an overnight culture of *S. pseudintermedius* ST71 was sub-cultured to an OD of 0.5 at 37° C. The bacteria were pelleted and re-suspended in fresh TSB. DCFDA was added to a final concentration of 20 μM to the bacterial culture incubated with various concentrations of extract (0-320 μg/ml) at 37° C. for 1 h. Fluorescence intensity was immediately measured at an excitation wavelength of 488 nm and an emission wavelength of 525 nm using a SpectraMax iD3 (Molecular Devices).

Bacterial Viability Assay

Dead or damaged bacteria induced by *S. felis* C4 extract were evaluated using the LIVE/DEAD BacLight Bacterial Viability Kit, according to manufacturer's instructions (Invitrogen, catalogue no. L7012). An overnight *S. pseudintermedius* ST71 culture was washed with fresh TSB and OD adjusted to 0.5 under treatment with increasing concentrations of extract (0, 0.8, 1.0, 1.6, 3.1, 12.5 μg/ml). After incubation for 4 hr, the bacteria were harvested, washed and resuspended in 1×PBS. Equal volumes of SYTO9 and propidium iodide (PI) were mixed and 3 μl was added to each sample to a final volume of 1 ml and incubated at room temperature in the dark for 15 min. Flow cytometry measurements were taken on a BioRad ZE5 Cell Analyzer with forward and side scatter parameters for detecting bacteria that were non-stained. Total bacteria were gated by dual stained but SYTO9-positive only population. The percentage dead or membrane-compromised bacteria were detected and recorded by the population that were SYTO9- and PI-positive. Analysis was performed using FlowJo V10 software (BD Biosciences).

Transmission Electron Microscopy

*S. pseudintermedius* ST71 cell pellets were immersed in modified Karnovsky's fixative (2% glutaraldehyde and 2% paraformaldehyde in 0.10 M sodium cacodylate buffer, pH 7.4) for at least 4 h and further postfixed in 1% osmium tetroxide in 0.1 M cacodylate buffer for 1 hr on ice. The cells were stained all at once with 2% uranyl acetate for 1 hr on ice, then dehydrated in a graded series of ethanol (50-100%) while remaining on ice. The cells were washed with 100% ethanol and washed twice with acetone (10 min each) and embedded with Durcupan. Sections were cut at 60 nm on a Leica UCT ultramicrotome, and picked up on 300 mesh copper grids. Sections were post-stained with 2% uranyl acetate for 5 minutes and Sato's lead stain for 1 minute. Grids were viewed using a JEOL JEM-1400Plus (JEOL, Peabody, MA) transmission electron microscope and photographed using a Gatan OneView 4K digital camera (Gatan, Pleasanton, CA).

Mouse Skin Colonization and Infection with *S. pseudintermedius*

Mouse skin colonization. All experiments involving live animal work were performed in accordance with the approval of the University of California, San Diego Institutional Animal Care and Use Guidelines (protocol no. S09074). For mouse skin challenge experiments involving *S. felis* strains and *S. pseudintermedius* ST71, the dorsal skin of hairless age-matched 8-10 week-old SKH1 mice (n=2, per treatment) were scrubbed with alcohol wipes and 5×10 6/cm$^2$ or 5×10$^7$/cm$^2$ CFU of overnight cultured *S. felis* C4, *S. felis* ATCC 49168 or *S. pseudintermedius* ST71 was inoculated onto 1×1 cm sterile gauze pads, which were placed onto the dorsal skin and secured with wound dressing film (Tegaderm [3M]) film for 72 h. For experiments involving live *S. felis* C4 bacteria or extract topical treatment, the dorsal skin of age-matched 8-10 week-old C57BL/6 mice (n=4, per treatment) was shaved and depilated by using Nair cream followed by removal with alcohol wipes. The skin was allowed to recover from hair removal for at least 24 h before the application of bacteria. Prior to bacterial challenge, the dorsal skin was tape-stripped and *S pseudintermedius* ST71 agar disks (3% tryptic soy broth [TSB], 2% agar; diameter 8 mm) containing 5×10$^7$ CFU was applied to the skin for 48 h, as previously described (Nakatsuji et al., 2016). The dorsal skin was covered with Tegaderm and a bandage was applied to hold the agar disk or gauze in place for the duration of the treatment. The bandage, Tegaderm and agar disk were removed and 5×10$^7$/cm$^2$ CFU of overnight cultured *S. felis* C4, or 150 µl of extract (10 mg/ml) or 3% TSB control, was inoculated onto 2×2 cm sterile gauze pads and applied to the infected site every 24 h for 72 h. After the treatment of mouse skin with live bacteria or extract, the dressing film and gauze pad were removed, and surface bacteria were collected using a swab soaked in TSB-glycerol solution. The swab head was then placed in 1 mL of TSB-glycerol solution, vortexed (30 seconds), serial-diluted, and plated onto Baird Parker agar plates supplemented with egg yolk tellurite for enumeration of coagulase-positive staphylococci (Carter, 1960) or mannitol salt agar plates for enumeration of all surface staphylococci (Parisi and Hamory, 1986).

Mouse infection and dermonecrosis model. The day prior to bacterial infection, the dorsal skin of age-matched 8-10 week old C57BL/6 mice (n=5, per treatment) was shaved and depilated by using Nair cream followed by removal with alcohol wipes. A 50 µl inoculum suspension containing 1×10$^7$ CFU of late log phase *S. pseudintermedius* ST71 in PBS was intradermally injected into the dorsal skin using 0.3 mL/31-gauge insulin syringe (BD, Franklin Lakes, NJ). At 1 h post-infection, a 50 µl suspension of the *S. felis* C4 extract (250 µg, at a concentration of 5 mg/ml in 25% DMSO) or a control suspension of 1×PBS in 25% DMSO was injected twice in two separate skin sites directly adjacent to the bacterial injection site. Body weights of the mice were measured before and after infection every day for 14 days. To determine lesion size, a ruler was positioned adjacent to the mouse skin lesions and digital photos were taken daily with a Kodak PIXPRO Astro Zoom AZ421 and analyzed via ImageJ software (National Institutes of Health Research Services Branch, Bethesda, MD, USA). Lesion size in mm 2 was measured by calculating the length×width.

Quantitative Real-Time PCR

RNA extracted from NHEK cells (Pure Link RNA isolation kit, Life Technologies, USA) was quantified on a Nanodrop 2000/200c spectrophotometer (Thermo Fisher, USA). Purified RNA (500 µg) was used to synthesize cDNA using the iScript™ cDNA Synthesis Kit (Bio-Rad, USA). Pre Developed Taqman® (Thermo Fisher, USA) and SYBR-Green gene expression assays (Integrated DNA Technologies, USA) were used to evaluate mRNA transcript levels.

RNA Sequencing

RNA was extracted from NHEK cells using a PureLink RNA mini kit (Life Technologies, USA). Isolated RNA was submitted to the UCSD IGM Genomics Center for RNA-sequencing performed on a high-output run V4 platform (Illumina, USA) with a single read 100 cycle runs. Data alignment was performed using Partek® Flow® genomic analysis software (Partek, USA) with Tophat2 (version 2.0.8) Gene ontology (GO) enrichment analysis was performed on differentially regulated genes (1.5-fold) using DAVID 6.8.

Statistical Analysis

Significant differences between the means of the different treatments were evaluated using GraphPad Prism version 7.03 (GraphPad Software, Inc., La Jolla, CA). Either unpaired, two-tailed Student's t test or one-way analysis of variance (ANOVA) followed by Dunnett's or Turkey's multiple comparisons test were used for statistical analysis and indicated in the respective figure legends. Differences were considered statistically significant with a p value of <0.05.

Screen of Animal-Derived Staphylococci Isolates Identified a Feline Skin Commensal Bacterium with Broad-Spectrum Antimicrobial Activity.

Figures 3A, 3B:
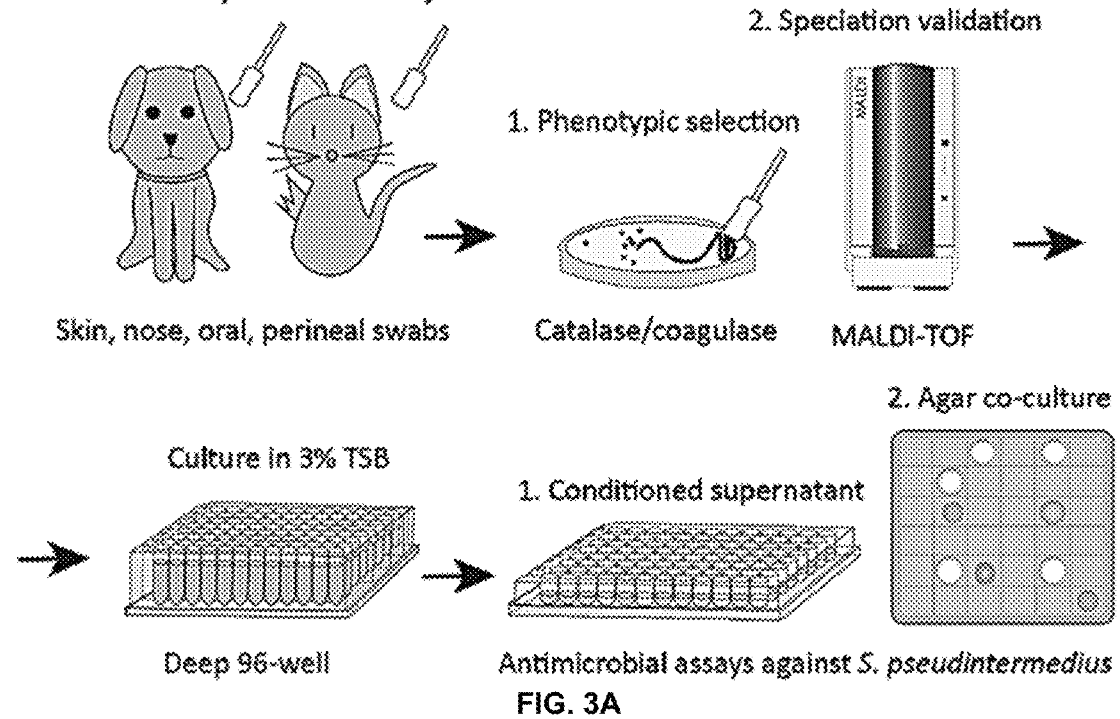
FIG. 3A-E shows screening and discovery of a feline skin commensal bacterium that inhibits drug-resistant gram-positive pathogens. (A) Illustration of the selection and screening strategy of animal-derived staphylococci against the growth of methicillin-resistant *S. pseudintermedius* (MRSP) ST71 in liquid culture and agar co-culture assays. (B) The panel of 58 feline and canine isolates selected for antimicrobial testing, including human-derived *S. hominis* A9 and *S. capitis* E12 positive control antimicrobial strains and the non-antimicrobial *S. aureas* 113 negative control. (C) Inhibition of *S. pseudintermedius* ST71 growth by OD600, relative to TSB control at 100%, after 18 h incubation in 50%, 25%, or 12.5% (1:1, 1:4, 1:8 ratio) sterile conditioned supernatant from all staphylococci isolates. Greater than 80% inhibition of growth was considered antimicrobial (AM+). (D) Images of the agar co-culture assay showing zone of inhibition (black circle surrounding colony) produced by all staphylococci test isolates against *S. pseudintermedius* ST71, including *S. felis* C4, N26, V13 (S. f C4, S. f N26, S. f V13), *S. pseudintermedius* N13 and Q13 (S. p N13 and S. p Q13), and positive control *S. hominis* A9 (S. h A9, all indicated by arrows). (E) Inhibition of bacterial growth relative to TSB alone at 100%, against select gram-positive and gram-negative pathogens after 18 h incubation (48 h incubation for *E. faecium*) in the presence of increasing amounts of sterile conditioned supernatant from *S. felis* C4 overnight growth. Error bars indicate SEM. Representative of three separate experiments.
Figure 3C:
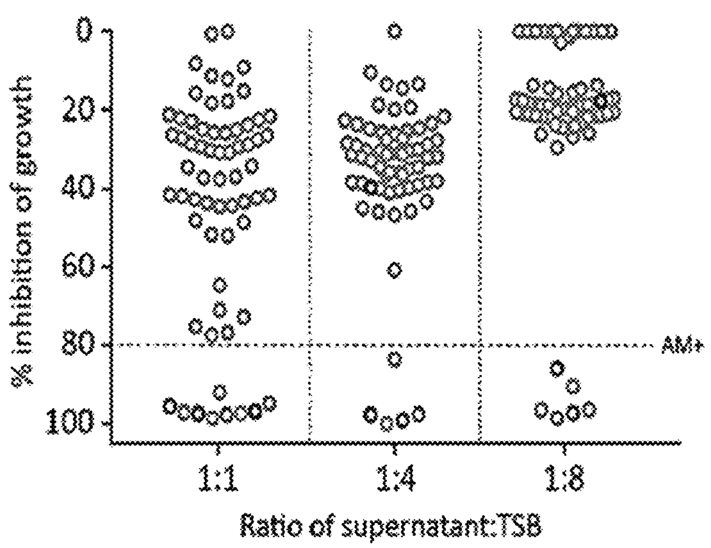
Figure 3D:
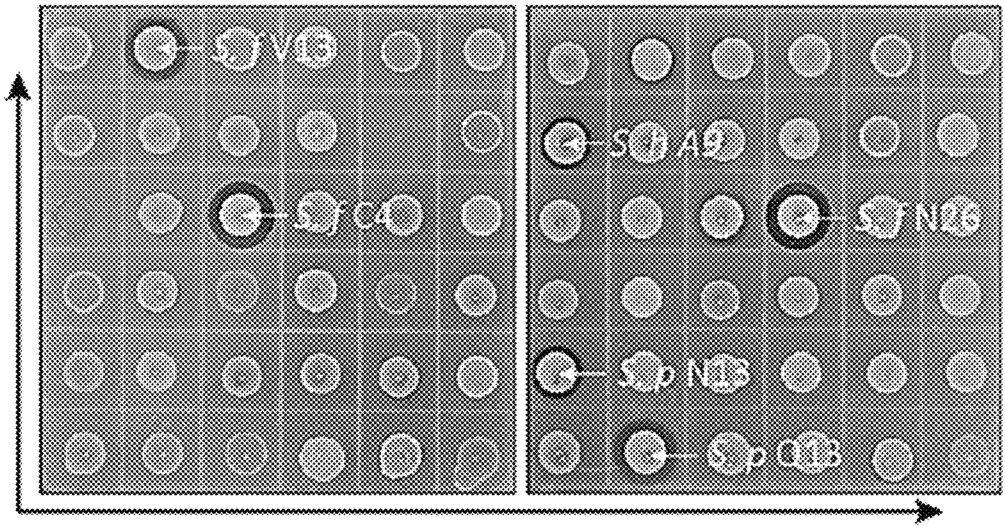
Figures 3E, 4A:
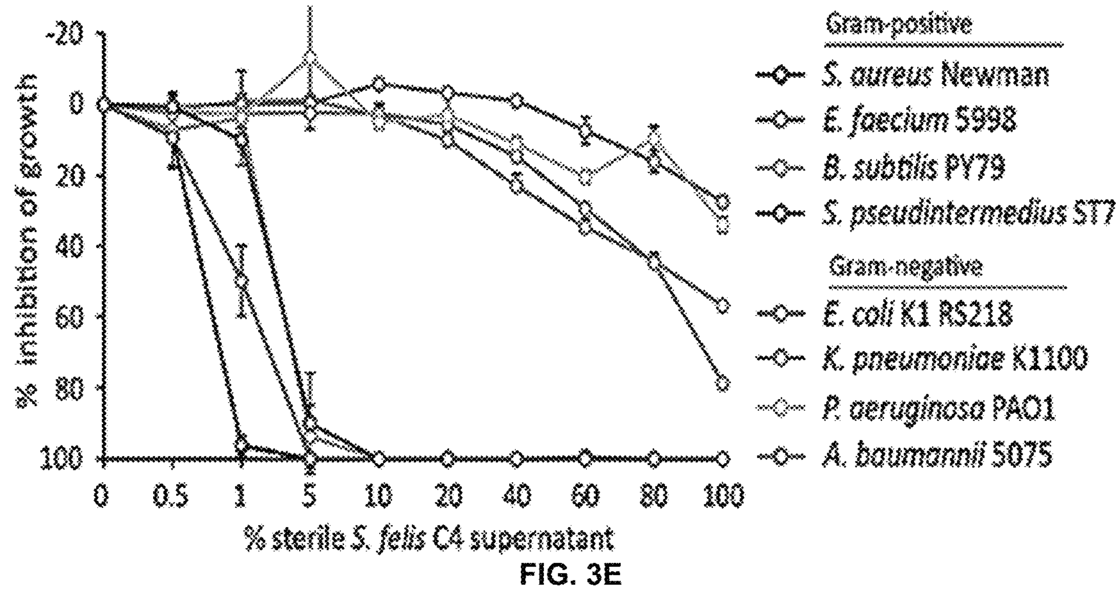
FIG. 4A-G shows live bacteriotherapeutic intervention with *S. felis* C4 protects against *S. pseudintermedius* colonization in mice. (A) Minimum inhibitory concentrations (MIC) of the indicated antibiotics against *S. felis* C4. (B) Representative images of the dorsal skin of 8-10 week-old SKH1 mice dorsal skin 3 days post-challenge with live *S. felis* C4, *S. pseudintermedius* ST71 or *S. felis* ATCC 49168, inoculated at the indicated amounts. n=2, per treatment group (C-E) $5\times10^7$ CFU/cm$^2$ of *S. pseudintermedius* ST71 was applied onto the back skin of C57BL/6 mice for 48 h and challenged with TSB, *S. felis* C4 extract (1 mg) or live *S. felis* C4 ($5\times10^7$ CFU/cm$^2$) for 72 h. Post-treatment, mouse back skin was photographed (C) and swabbed to enumerate *S. pseudintermedius* ST71 (S. pseud. ST71) CFU on selective Baird-Parker egg yolk tellurite agar (D) or total staphylococci CFU on selective mannitol-salt agar plates (E). n=3 for TSB and n=4 for extract and *S. felis* C4. Error bars indicate SEM. One-way ANOVA with multiple comparisons (Dunnett's correction) was performed. p values: *p<0.05; (F-G) At day 0, $1\times10^7$ CFU of *S. pseudintermedius* ST71 was intradermally injected into the back skin of 8-10 week-old C57BL/6 mice and at 1 h post-infection two inoculations of *S. felis* C4 extract (250 μg) or PBS/25% DMSO control were injected adjacent to the infection site. (F) Representative images of *S. pseudintermedius* ST71-induced dermonecrosis over time after receiving control PBS/DMSO or *S. felis* C4 extract. (G) Quantification of lesion size (mm 2) over time as measured by L×W of lesions. n=4 for DMSO/PBS and n=5 for extract. Error bars indicate SEM. A two-tailed, unpaired Student's t-test was performed. p values: *p<0.05; p<0.01; *p<0.001.

Experiments were performed to determine whether commensal staphylococci collected from the skin, nasal, oral and perineal sites of companion dogs and cats exhibit antimicrobial activity against methicillin-resistant *S. pseudintermedius* (MRSP) ST71 (FIG. 3A). Fifty-eight *staphylococcus* isolates across the coagulase-positive (CoPS) and coagulase-negative (CoNS) groups were screened, including validated antimicrobial strains of human origin, *S. hominis* A9 (Nakatsuji et al., 2017) and *S. capitis* E12 (O'Neill et al., 2020) and a non-active *S. aureas* 113 negative control strain (FIG. 3B). The animal test isolates were screened for antimicrobial activity by live co-culture on agar plates or in the presence of sterile conditioned supernatant, as illustrated in FIG. 3A. Amongst all test isolates, five strains demonstrated greater than 80% inhibition of *S. pseudintermedius* growth (dashed line) across all three different dilutions of supernatant (1:1, 1:4, 1:8) (FIG. 3C). Surprisingly, these strains exhibited greater potency compared to the positive control *S. hominis* A9 supernatant (indicated by black circle), which inhibited growth of *S. pseudintermedius* in a 1:1 dilution, but not at 1:4 or lower. Amongst the five positive hits, three were identified as *S. felis* and two *S. pseudintermedius*. In the second independent antimicrobial assay, all five isolates including positive control *S. hominis* A9, produced an observable zone of inhibition against *S. pseudintermedius* during live co-culture on agar (FIG. 3D). The two feline *S. felis* species (C4, N26 labelled with white arrows) produced the largest inhibitory zones, extending 3.0-3.3 mm outward from the edge of the growing colony. The *S. felis* C4 strain was chosen for further analysis, as it demonstrated potent activity and was isolated from healthy skin. To investigate the significance and selectivity of the *S. felis* antimicrobial supernatant, we tested its capacity to inhibit the growth of other clinically relevant, gram-positive and gram-negative pathogens (of which several belong to the clinically-relevant ESKAPE group). Of the four gram-negative strains tested, only moderate inhibition was demonstrated after 18 h incubation with 80-100% undiluted *S. felis* C4 supernatant (FIG. 3E). In contrast, culture with just 1-5% of *S. felis* C4 supernatant was sufficient to inhibit >80% growth of all four gram-positive organisms, including *S. pseudintermedius, E. faecium, B. subtilis* and *S. aureas.*

Of the three antimicrobial *S. felis* isolates, only the C4 supernatant retained activity after precipitation with 75% ammonium sulfate (AS) (FIG. 7A). Moreover, 75% AS was highly effective in precipitating the antimicrobial factor(s) from the C4 supernatant since no activity could be visualized in the non-precipitate fraction (FIG. 7B). This effect was also achieved with a simpler extraction by n-butanol. The antimicrobial butanol extract remained active at room temperature (RT), up to one week and was stable after boiling (FIG. 7C). As expected, the butanol extraction provided a partially purified and enriched antimicrobial fraction compared to crude supernatant and AS precipitation (FIG. 7D). Therefore, further experiments involving the *S. felis* C4 extract describes sterile supernatant obtained via n-butanol extraction. Interestingly, the antimicrobial activity of *S. felis* C4 was sufficient to disrupt bacterial biofilms. Reports have shown that most clinically-derived *S. pseudintermedius* strains are biofilm producers (Singh et al., 2013). Biofilm formation is considered an important determinant of staphylococci virulence and is associated with increased skin colonization and severity of disease (Di Domenico et al., 2018; Kwiecinski et al., 2015). A 4 h preformed biofilm of pseudintermedius ST71 showed a significant decrease in crystal violet (CV) staining over time, when incubated with 100% conditioned supernatant of *S. felis* C4, indicating biofilm disruption and degradation (FIG. 8A). Importantly, the *S. felis* C4 extract also exhibited similar anti-biofilm activity as crude conditioned supernatant, with biofilm mass reduced by 48% at 250 μg/ml and 58% at 500 μg/ml (FIG. 8B).

Figures 4B, 4C:
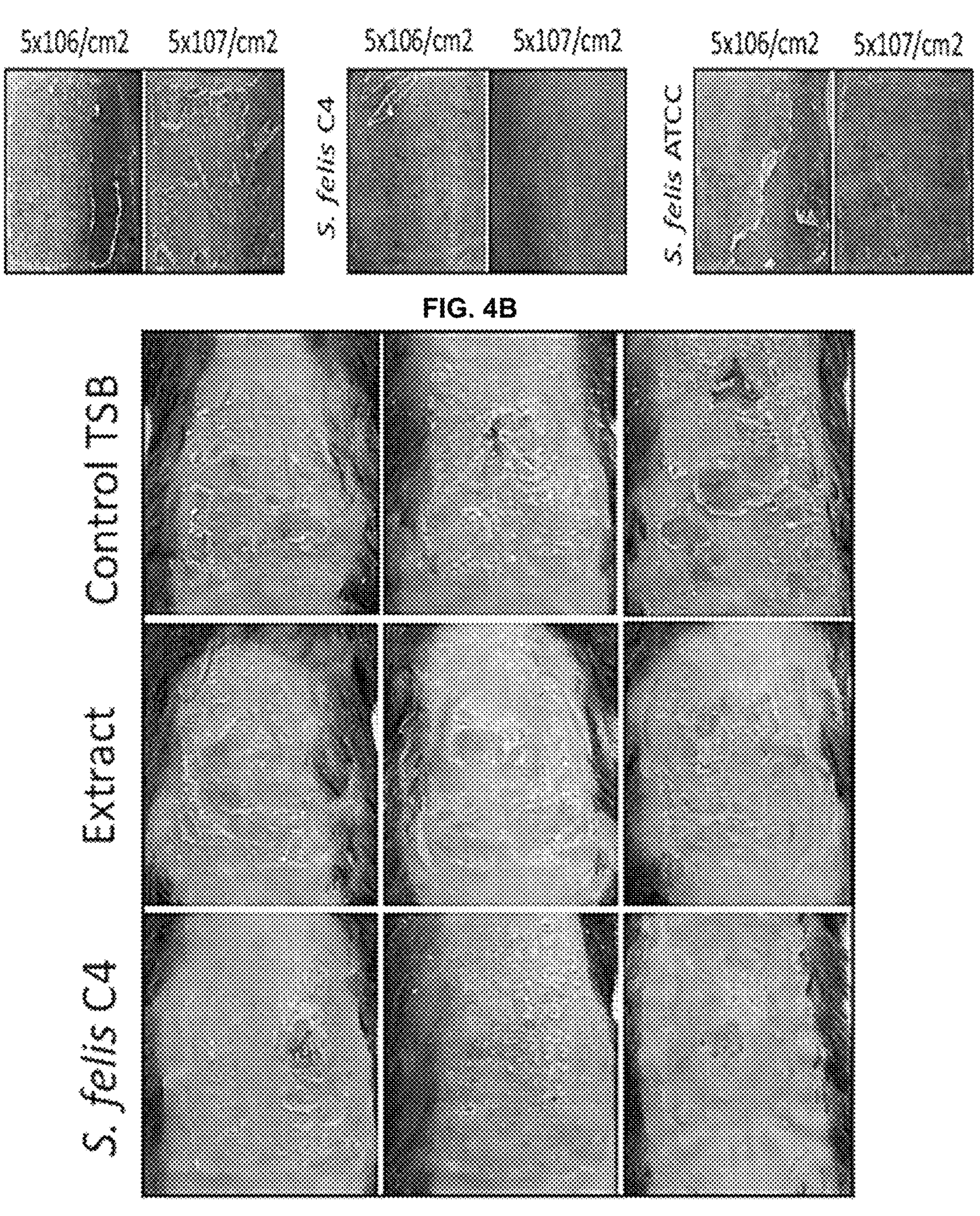

*S. felis* C4 Inhibits *S. pseudintermedius* Skin Colonization and Infection in Mice Experiments were performed to investigate the translational potential of *S. felis* C4 and its antimicrobial products as a potential therapy against *S. pseudintermedius* colonization and infection. Since *S. felis* C4 is a commensal bacterium that was isolated from healthy feline skin, we speculated it should be safe and well tolerated on mouse skin. *S. felis* C4 was found to be sensitive to several common antibiotics (FIG. 4A) and as such represents a suitable strain for further investigation as a bacteriotherapy. We therefore assessed the skin tolerability of a 3-day topical application of *S. felis* C4 on SKH1 hairless mice. Whereas *S. pseudintermedius* and the non-antimicrobial *S. felis* ATCC 49168 induced evidence of scaling and redness on mouse back skin, *S. felis* C4 did not promote any adverse reaction (FIG. 4B).

Figures 4D, 4E, 4F:
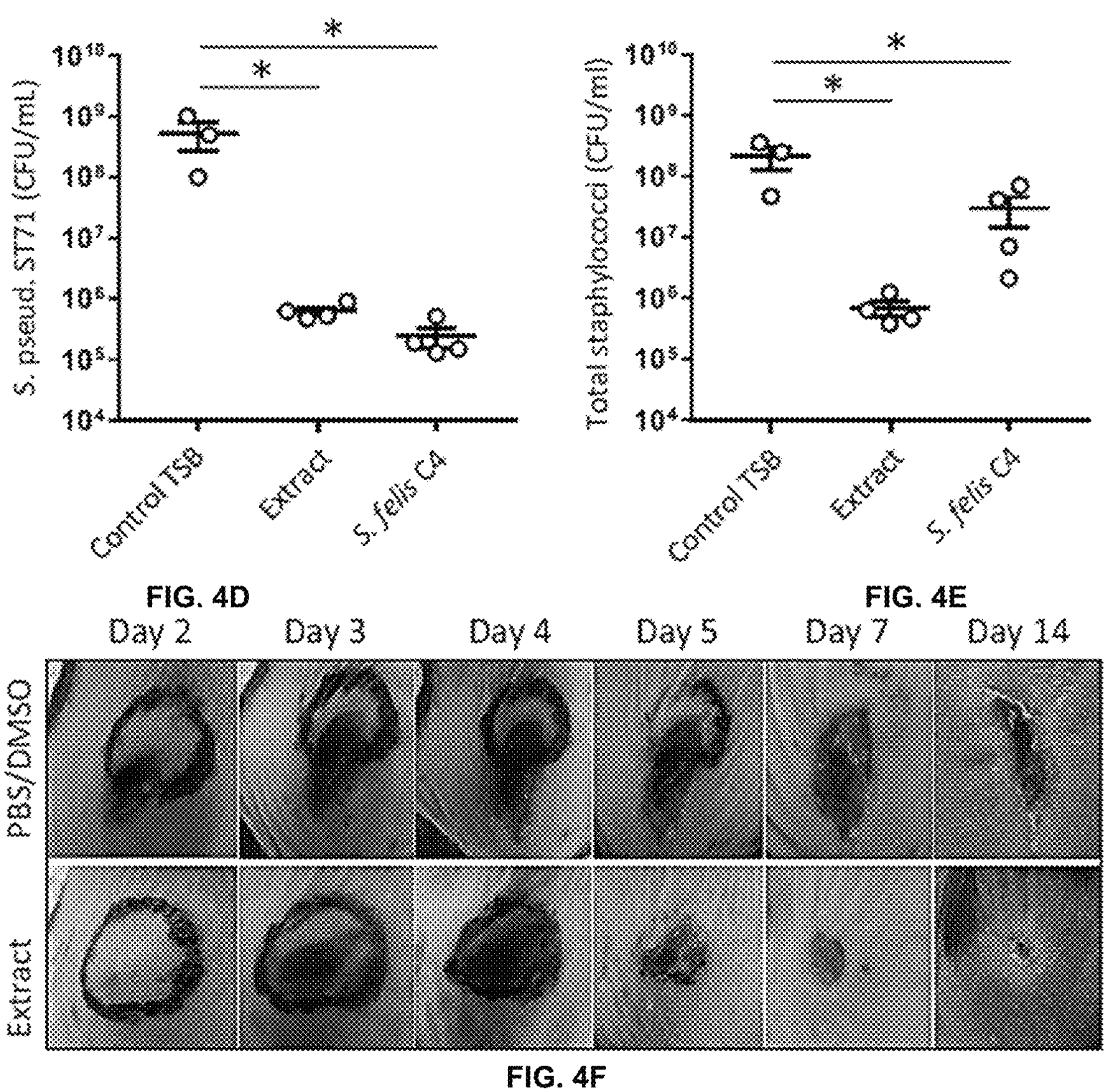
Figures 4G, 5A:
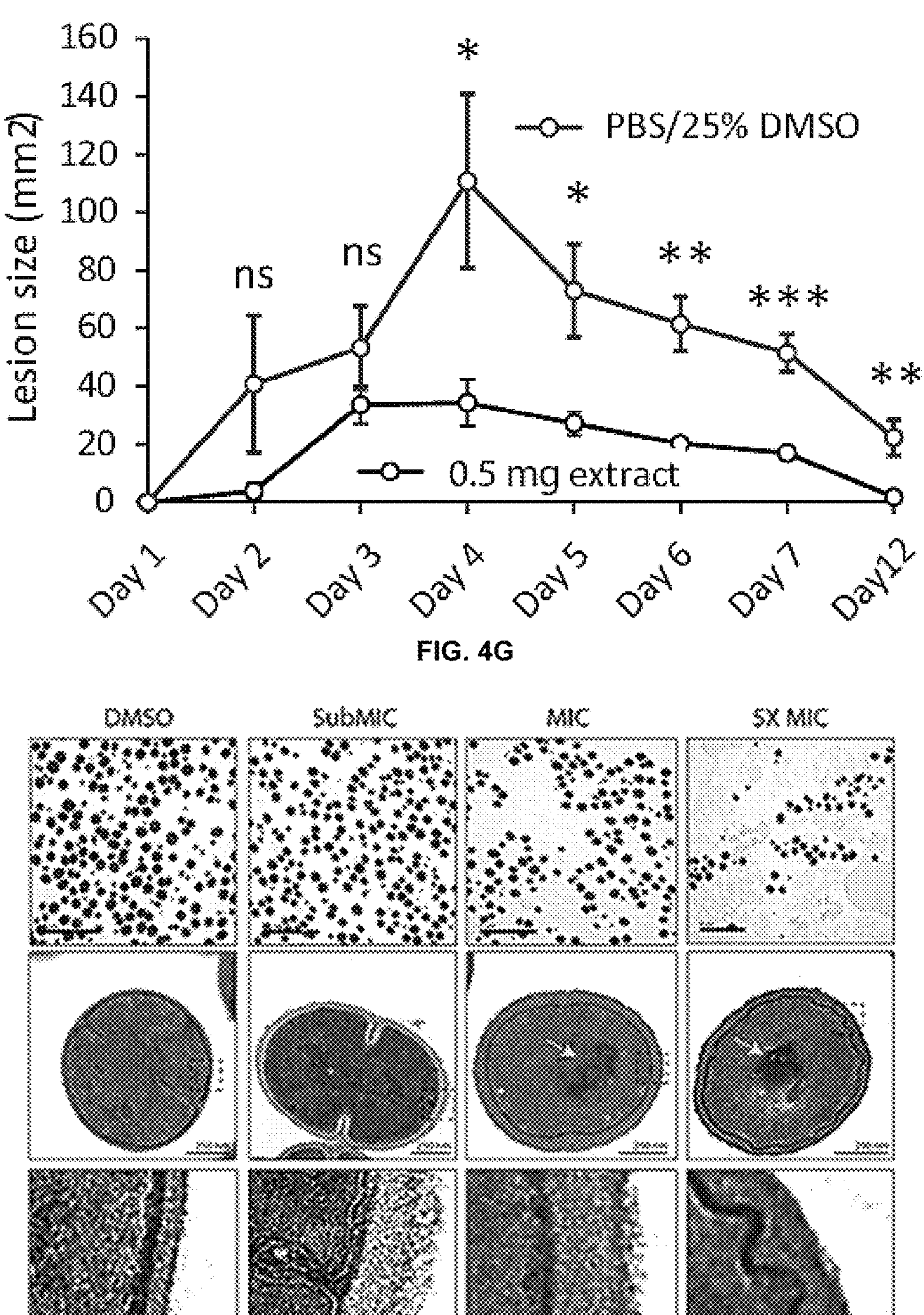
FIG. 5A-D shows *S. felis* C4 extract contains a membrane-active antibacterial molecule. (A) TEM images of *S. pseudintermedius* ST71 after 1 h treatment with DMSO control or *S. felis* C4 extract at indicated concentrations. Yellow arrows indicate evidence of condensed DNA. Lower image panels represent higher magnification of regions highlighted by dashed black boxes. Scale=250 nm (B) Total ROS accumulation in *S. pseudintermedius* ST71 after 1 h treatment in increasing concentrations of *S. felis* C4 extract. Error bars indicate SEM. (C) Total intracellular ATP accumulation in *S. pseudintermedius* ST71 after 1 h treatment in increasing concentrations of *S. felis* C4 extract. Error bars indicate SEM. (D) Live/dead fluorescent images of *S. pseudintermedius* ST71 after 1 h treatment with DMSO control or extract at indicated concentrations. Viable bacterial cells were stained green by SYTO9 and damaged/dead cells were stained red by PI. Scale=10 μm. (B), (C) representative of three separate experiments.

To test the antimicrobial activity of *S. felis* C4 on skin, $5\times10^7$ CFU/cm$^2$ *S. pseudintermedius* was applied directly onto mouse back skin for 48 h, then applied an equal density of *S. felis* C4 or 1 mg of extract to the infected site. This was repeated daily for three days. The back skin showed a reduction in scaling and redness post-treatment with *S. felis* C4 and extract compared to control (FIG. 4C). More importantly, this correlated with a significant 850-fold decrease in *S. pseudintermedius* ST71 CFU following extract application and 2178-fold decrease following live *S. felis* C4 application (FIG. 4D). Plating of CFU onto selective media once again confirmed that the extract treatment significantly reduced bacterial colonization (FIG. 4E). In contrast, no significant difference in staphylococci CFU counts were recorded between the control group and *S. felis* C4 application, suggesting that the *S. felis* bacteria colonized and outcompeted *S. pseudintermedius* ST71 on skin. To further investigate the potential of the *S. felis* C4 extract as an anti-MRSP intervention, its efficacy in limiting the infectious outcome of cutaneous challenge with *S. pseudintermedius* ST71 was evaluated. An inoculum of $1\times10^7$ CFU *S. pseudintermedius* ST71 was intradermally administered into the back skin of mice. At 1 h post-infection, two intradermal inoculations of 250 μg extract were administered adjacent to the infection site and necrosis was monitored by measuring lesion size for 14 days. Compared to controls, the extract-treated mice exhibited slower lesion progression from day 1 to 2, and significantly better protection from *S. pseudintermedius* skin disease from day 4 (FIG. 4F-G). These results demonstrate the in vivo efficacy and clinical potential for *S. felis* C4 as a bacteriotherapy against *S. pseudintermedius* skin colonization and infection.

Antimicrobial *S. felis* C4 Promotes Disruption of the Bacterial Membrane.

Figures 5B, 5C, 5D, 6A:
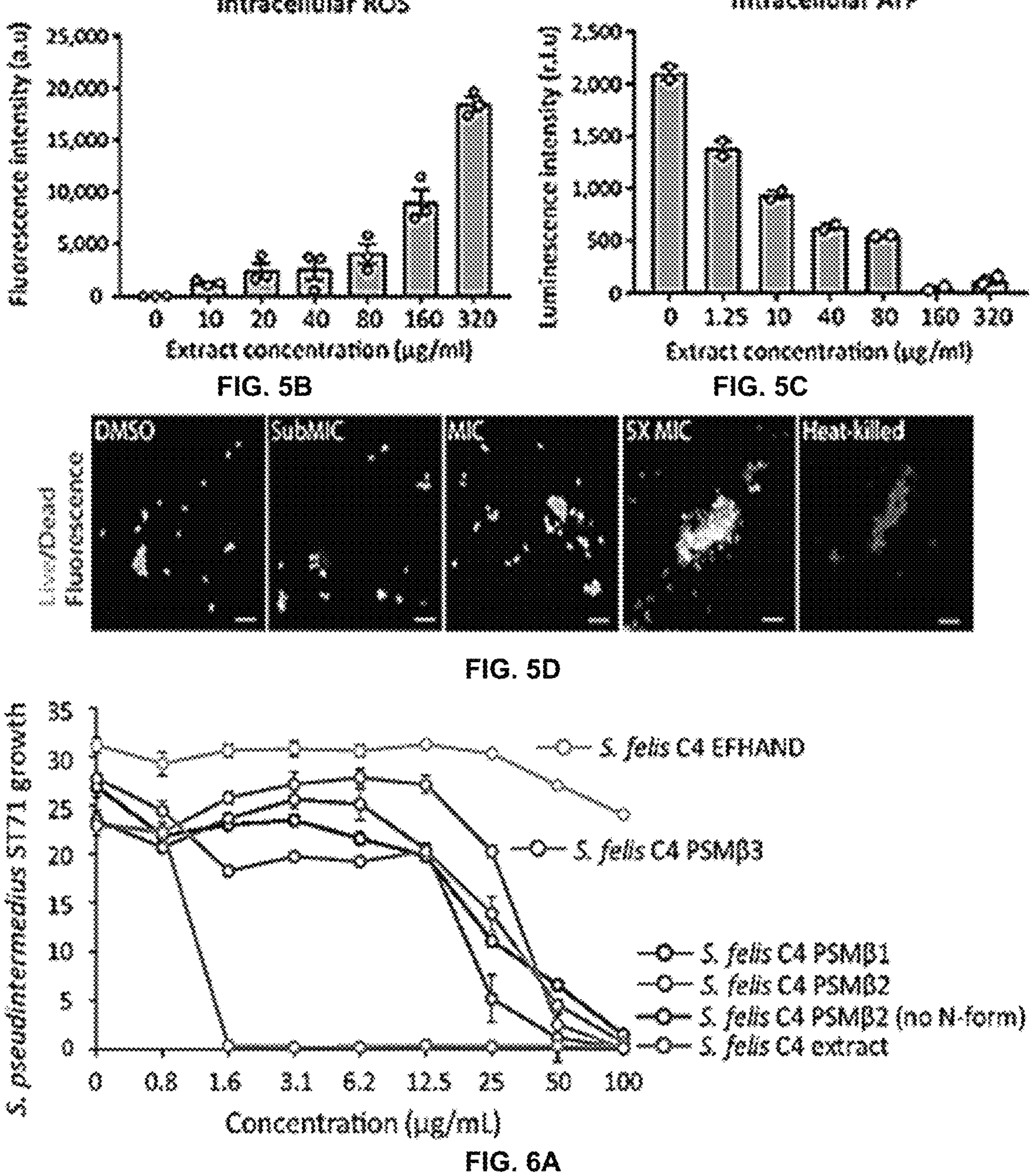
FIG. 6A-G shows antimicrobial *S. felis* C4 extract and PSMβ suppress TLR-mediated inflammation. (A) Growth of *S. pseudintermedius* ST71 after 18 h incubation with increasing concentrations of synthetic formylated PSMβ peptides (PSMβ1, PSMβ2, PSMβ3), or synthetic peptide containing an EF-hand domain (Unknown EF-hand). (B) Lactate dehydrogenase (LDH) release in NHEKs after 24 h treatment with *S. felis* C4 extract, *S. felis* PSMβ2, PSMβ3 or positive control cytotoxic PSMα from *S. aureas* or PSMγ from *S. epidermidis*. Percentage (%) cytotoxicity measured by maximum LDH release into supernatant collected after untreated cell freeze thaw. (C) mRNA transcript abundance measured by qPCR in NHEKs stimulated with or without TLR2/6 agonist MALP-2 (200 ng/ml) or TLR3 agonist Poly I:C (0.4 μg/ml) in the presence or absence of *S. felis* C4 extract, PSMβ2 or PSMβ3 (10 μg/ml) or DMSO control (0.1%) at 4 h post-treatment. (D) Quantification of CXCL10 protein by ELISA from supernatant of NHEKs stimulated with MALP-2 or Poly I:C in the presence of *S. felis* extract or PSMβ2, PSMβ3 or DMSO control 24 h post-treatment. (E) Time-course of the TLR3 signaling cascade by immunoblot of phosphorylated TBK1 and IRF3 proteins after stimulation of NHEKs with Poly I:C, DMSO, or co-treatment with Poly I:C and PSMβ2. (F) Gene ontology (GO) pathway analysis of genes downregulated in NHEKs after 4 h co-treatment with Poly I:C and PSMβ2 versus treatment with Poly I:C alone. (G) Hierarchical clustering and Heatmap visualization of selected genes from GO enriched 'immune response' pathway (1.5-fold change) 4 h post-treatment with DMSO, PSMβ2 or Poly I:C alone or with PolyI:C and PSMβ2 cotreatment. (A-D) error bars indicate SEM. Representative of at least three separate experiments. One-way ANOVA with multiple corrections (Turkey correction) was performed. p values: * $p<0.05$;  $p<0.01$; * $p<0.001$.

Next, experiments were performed to better understand how the antimicrobial action of *S. felis* C4 negatively affects bacterial physiology. Given the selective nature of the *S. felis* C4 supernatant against gram-positives (FIG. 3E), it was speculated that *S. felis* C4 activity may target and compromise the bacterial membrane and/or cell wall. To address this question, transmission electron microscopy (TEM) imaging was conducted on sectioned *S. pseudintermedius* ST71 bacteria exposed to 1 h treatment with control DMSO (1%), sub-MIC (1 μg/ml), MIC (8 μg/ml) or 5×MIC (40 μg/ml) extract concentrations (FIG. 5A). TEM observations upon control DMSO treatment showed normal, uniform spherical cocci physiology and septum formation indicating active replication. In contrast, short exposure to the extract resulted in drastic changes to the bacterial ultrastructural morphology, with evidence of cell wall thickening and alterations in the structure and rigidity of the cell membrane (FIG. 5A, lower zoom inset panels). Moreover, treatment with extract showed evidence of greater chromosomal compaction compared to control, evidenced by the increased (electron) density of the nucleoid (highlighted yellow arrows). Additional evidence supporting a role for *S. felis* C4 in promoting bacterial membrane damage was provided by several in vitro microbial cell viability assays. From mid-log phase cultures of *S. pseudintermedius* ST71 30 min post-treatment with the extract, a dose-dependent increase in reactive oxygen species (ROS) (FIG. 5B) coincided with a concomitant decrease in intracellular ATP levels (FIG. 5C). Further evidence for a membrane-active antimicrobial was provided by increased dual staining of SYTO9-positive bacteria (green) with the membrane-impermeable dye propidium iodide (PI) (red). After treatment with 5×MIC of extract, a proportion of bacterial cells showed dual staining, with entry of PI likely reflecting a loss of membrane integrity (FIG. 5D).

Purification and Identification of PSMβ Peptides as Antimicrobial Products of *S. felis* C4.

To determine the nature of the antimicrobial product produced by *S. felis* C4, sterile supernatant was purified by HPLC. This yielded two major peaks that eluted at 55% and 57% acetonitrile (FIG. 9A). Anti-*S. pseudintermedius* activity was predominantly associated with fraction 32 which eluted at 55% acetonitrile (FIG. 9B). SDS PAGE and silver stain of fraction 32 and neighboring inactive fractions revealed a unique band of roughly 5 kDa in size (FIG. 9C). To determine if this small protein was responsible for antimicrobial activity, gel slices of the fraction 32 lane corresponding to small, medium and larger proteins (5 kDa, 5-20 kDa and 20-50 kDa, respectively) were excised and extracted by acetone precipitation, as previously described (Botelho et al., 2010; Zhang et al., 2015). Only the ≤5 kDa band demonstrated antimicrobial activity after incubation with *S. pseudintermedius* (FIG. 9D), thereby suggesting the likely candidate to be a small peptide. Mass spectrometry (MS) analysis of the top 8 hits in the active and non-active fractions identified several putative small antimicrobial peptides (AMP), representing the phenol soluble modulin beta (PSMβ1-3) and gamma (PSMγ, aka delta-hemolysin) families and a peptide of unknown function containing a EF-hand domain, common amongst some antimicrobial $Ca^{2+}$ binding proteins, such as S100A8/S100A9 (Chazin, 2011) (FIG. 9E). Whole genome analysis of the *S. felis* C4 strain confirmed the presence of three PSMβ-encoding genes (FIG. 9F). Like some mammalian cationic AMPs such as cathelicidin LL-37, the PSMβ and EF-hand domain peptides have an α-helical amphipathic-like formation, a structural motif conserved in the recognition and binding of biological membranes (FIG. 9G). To determine if the peptides identified by MS exhibited antimicrobial activity, synthetic versions of all three *S. felis* PSMβ1-3 and the EF-hand domain containing peptide were tested. Interestingly, all three PSMβ peptides inhibited *S. pseudintermedius* growth at a concentration of 50 μg/ml (FIG. 6A). In contrast, the EF-hand domain-containing peptide did not inhibit bacterial growth up to 200 μg/ml. These results suggest that PSMβ peptides could be mediating the antimicrobial activity of *S. felis* C4.

*S. felis* C4 Extract and PSMβ Peptides Exhibit Anti-Inflammatory Activity by Suppressing TLR-Mediated Inflammation.

Figures 6B, 6C, 6D:
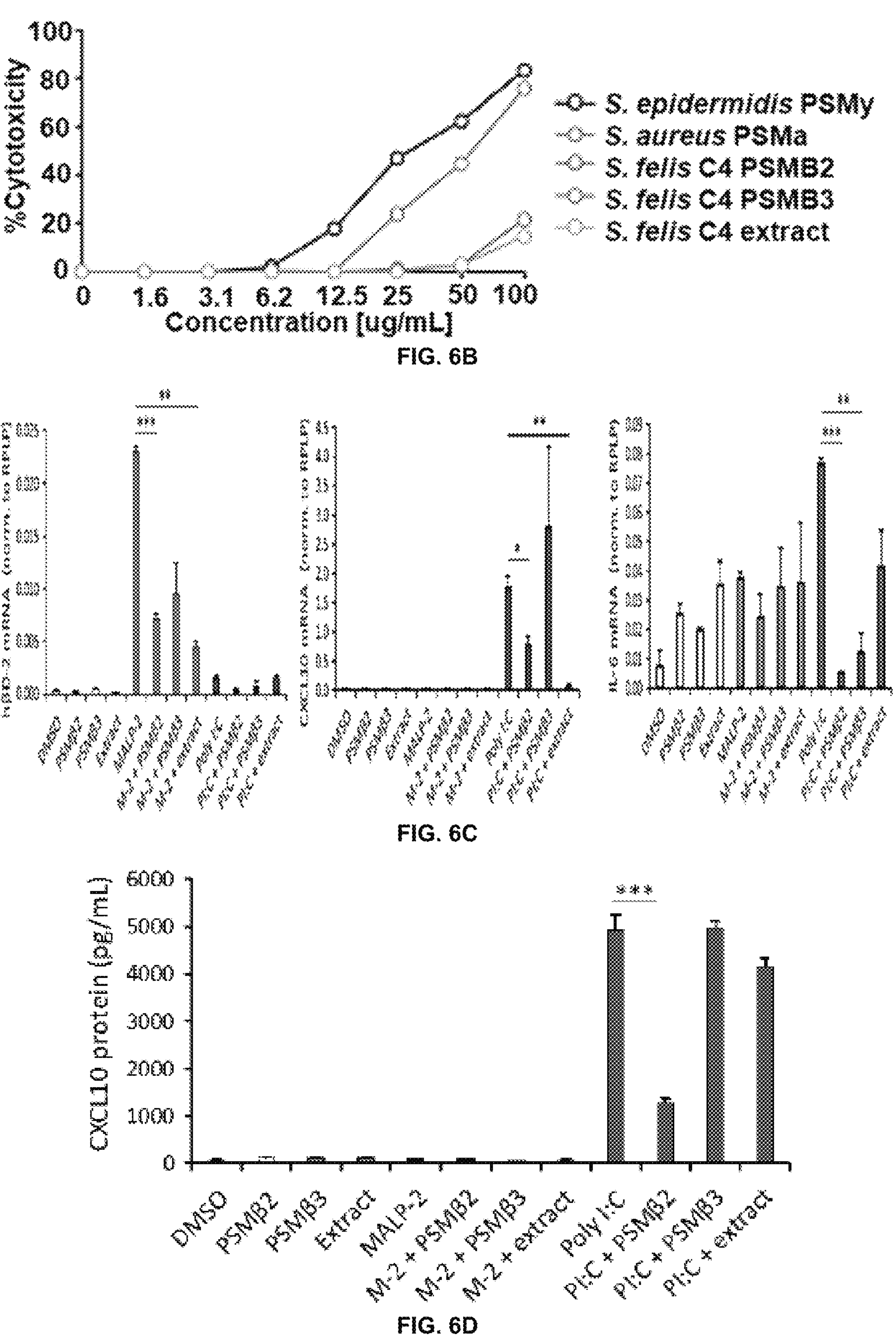

Unlike the well characterized cytolytic and inflammatory activities of PSMα, a defined role for PSMβ in mediating host interactions has been largely unexplored (Da et al., 2017). Based on our previous observation that *S. felis* C4 was well tolerated on murine skin, we asked if the antimicrobial extract and individual PSMβs would be tolerated by human keratinocytes. Primary normal human keratinocytes (NHEK) were treated with increasing concentrations of different PSMs for 24 h and cytotoxicity determined by quantifying LDH release. As expected, the hemolytic toxins PSMα and PSMγ were found to be highly cytotoxic whereas *S. felis* PSMβ2, PSMβ3, and the extract resulted in less than 5% LDH release at the antimicrobial concentration of 50 μg/ml (FIG. 6B).

Figure 6E:
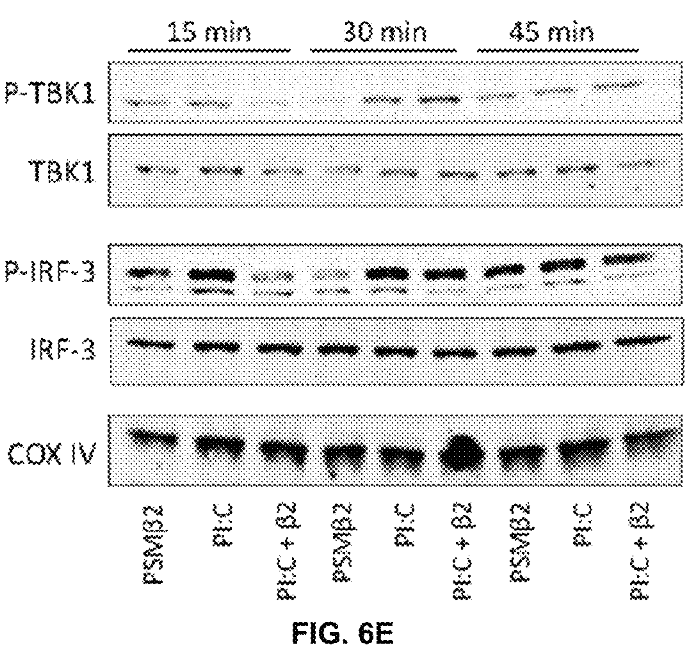
Figure 6F:
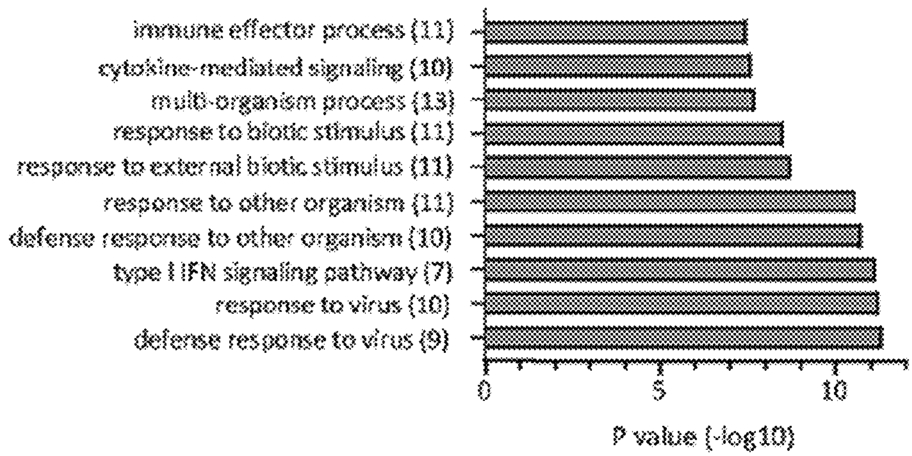
Figure 6G:
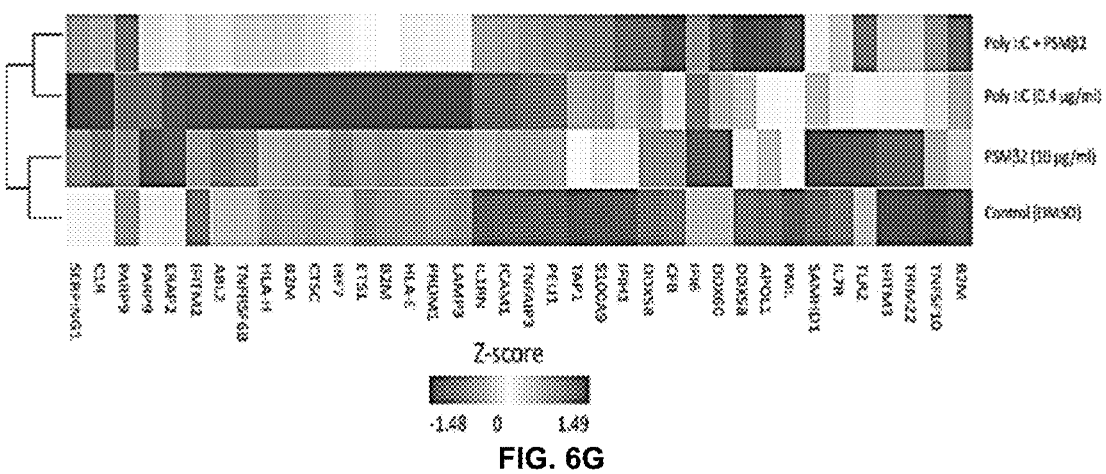

To investigate the potential effects of *S. felis* C4 on the host immune response, cells were stimulated with various TLR agonists in the presence or absence of the extract or the individual PSMs and measured inflammatory gene expression. NHEKs were treated with *S. felis* PSMβ2, PSMβ3, extract, DMSO control alone, or each in combination with the TLR2 agonist MALP-2 (200 ng/μl) or the TLR3 agonist Poly I:C (0.4 μg/ml) for 4 h. Neither PSMβ nor the extract resulted in any detectable increase in gene expression, whereas MALP-2 significantly increased the expression of hBD-2, and Poly I:C significantly increased CXCL10 and IL-6 expression (FIG. 6C). Interestingly, these TLR-mediated responses were significantly reduced during co-treatment with PSMβ or extract. This result was confirmed by ELISA, showing that PSMβ2 had a significant effect on suppressing CXCL10 secretion in NHEKs after 24 h co-treatment (FIG. 6D). To determine if this interaction is specific for epithelial cells, we also stimulated human THP-1 macrophage-like cells with MALP-2, or the TLR4 agonist LPS and found that IL-6 and TNFα expression was decreased during co-treatment with PSMβ2 (FIG. 10). The addition of PSMβ2 to NHEK activated by poly I:C demonstrated that PSMβ2 inhibited phosphorylation of TBK1 and IRF3 at 15 min post-stimulation with the peptide (FIG. 6E). This inhibition of inflammatory target gene and kinase activity was further evaluated by the analysis of changes in global gene expression using RNA-Seq analysis of NHEKs stimulated with Poly I:C, with and without PSMβ2 at 4 h and 24 h. Gene ontology (GO) analyses revealed the significant down-regulation of several gene clusters associated with 'immune effector process' and 'type I IFN signaling' at 4 h during co-treatment of PSMβ2 and Poly I:C (FIG. 6F). A heatmap of selected genes within the 'Immune response' GO term at 4 h post-treatment further highlighted the suppressive effect, but more significantly, showed that PSMβ2 treatment alone did not induce an immunological response in NHEKs (FIG. 6G). However, when NHEKs were treated with PSMβ2 in the absence of an inflammatory stimulus, we identified the downregulation of genes within GO terms such as "response to interleukin-1" (FIG. 11A) and "pathogenic *E. coli* infection" (FIG. 11B), suggesting that exposure to PSMβ2 primes cells to dampen potential inflammatory mediators in response to bacterial ligands. This contrasted with PSMβ2-upregulated genes which were mostly associated with biosynthetic pathways including lipid and amino acid metabolism.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising a peptide having the sequence of SEQ ID NO:3, or a sequence that includes 1 to 5 amino acid substitutions to SEQ ID NO:3, and at least one peptide selected from the group consisting of SEQ ID NO:4, 5 and 6, a pharmaceutically acceptable carrier for formulation as a lotion, ointment cream, powder, unguent, oil or spray, and wherein the composition inhibits or kills *S. aureas* and/or *S. pseudintermidius.*

2. The composition of claim 1, wherein the composition is a thickened topical formulation.

3. The composition of claim 1, wherein the composition is prepared for application to a surface.

4. A method for treating skin or mucosal infection in a subject comprising contacting the subject with an effective amount of a composition of claim 1.

5. The method of claim 4, wherein the skin or mucosal infection comprises an infection by *S. aureas* and/or *S. pseudintermidius.*

6. A method of treating skin or mucosal infections in a mammal by applying to the skin or mucosa an effective amount of the composition of claim 1 to a subject in need thereof.

7. The method according to claim 6, wherein the composition is applied topically.

8. A method of treating a bacterial infection in an animal or human, the method comprising exposing an infected area of the animal or human to composition of claim 1.

9. The method as claimed in claim 8, wherein the bacterial infection is an infection by *S. aureas* and/or *S. pseudintermidius.*

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Peptide Spacer/Linker
```

```
<400> SEQUENCE: 1

Gly Gly Gly Gly Ser
1               5


<210> SEQ ID NO 2
<211> LENGTH: 22
<212> TYPE: PRT
<213> ORGANISM: Artificial Sequence
<220> FEATURE:
<223> OTHER INFORMATION: Peptide Spacer/Linker

<400> SEQUENCE: 2

Gly Gly Gly Gly Gly Gly Ser Met Phe Gly Gly Ala Lys Lys Arg Ser
1               5                   10                  15

Gly Gly Gly Gly Gly Gly
            20


<210> SEQ ID NO 3
<211> LENGTH: 43
<212> TYPE: PRT
<213> ORGANISM: Staphylococcus felis

<400> SEQUENCE: 3

Met Ser Gly Leu Ile Asp Ala Ile Lys Thr Thr Val Glu Ala Gly Leu
1               5                   10                  15

Asn Gly Glu Trp Ala Asp Met Gly Leu Gly Ile Ala Glu Ile Val Ala
            20                  25                  30

Lys Gly Ile Glu Ala Ile Ser Gly Phe Phe Gly
        35                  40


<210> SEQ ID NO 4
<211> LENGTH: 43
<212> TYPE: PRT
<213> ORGANISM: Staphylococcus felis

<400> SEQUENCE: 4

Met Ser Asp Leu Ile Asn Ala Ile Lys Thr Thr Val Glu Ala Gly Leu
1               5                   10                  15

Asn Gly Glu Trp Thr Asp Met Gly Phe Gly Ile Ala Asp Ile Val Ala
            20                  25                  30

Lys Gly Ile Asp Val Ile Leu Gly Phe Phe Gly
        35                  40


<210> SEQ ID NO 5
<211> LENGTH: 43
<212> TYPE: PRT
<213> ORGANISM: Staphylococcus felis

<400> SEQUENCE: 5

Met Ser Asp Leu Ile Asn Ala Ile Lys Thr Thr Val Glu Ala Gly Leu
1               5                   10                  15

Asn Gly Glu Trp Thr Asp Met Gly Phe Gly Ile Ala Asp Ile Val Ala
            20                  25                  30

Lys Gly Ile Asp Val Ile Leu Gly Phe Phe Gly
        35                  40


<210> SEQ ID NO 6
<211> LENGTH: 43
<212> TYPE: PRT
<213> ORGANISM: Staphylococcus felis

<400> SEQUENCE: 6
```

```
Met Ala Asp Leu Ile Asn Ala Ile Lys Thr Thr Val Glu Ala Gly Leu
1               5                   10                  15

Asn Gly Glu Trp Thr Asp Met Gly Phe Gly Ile Ala Asp Ile Val Ala
            20                  25                  30

Lys Gly Ile Asp Val Ile Ser Gly Phe Phe Gly
        35                  40


<210> SEQ ID NO 7
<211> LENGTH: 25
<212> TYPE: PRT
<213> ORGANISM: Staphylococcus felis

<400> SEQUENCE: 7

Met Ala Ala Asp Ile Ile Ser Thr Ile Gly Asp Leu Val Lys Trp Ile
1               5                   10                  15

Ile Asp Thr Val Asn Lys Phe Lys Lys
            20                  25


<210> SEQ ID NO 8
<211> LENGTH: 52
<212> TYPE: PRT
<213> ORGANISM: Staphylococcus felis

<400> SEQUENCE: 8

Met Ser Lys Leu Thr Arg Val Ile Val Thr Ser Ile Met Thr Val Gly
1               5                   10                  15

Phe Leu Thr Ala Thr Leu Gly Leu Thr Ala Gly Asn Ala Asp Ala Lys
            20                  25                  30

Leu Glu Gly Asn Gly Thr Leu Ser Gln Lys Gln Tyr Gln Arg Leu Ala
        35                  40                  45

Ser Gln Gln Phe
    50


<210> SEQ ID NO 9
<211> LENGTH: 170
<212> TYPE: PRT
<213> ORGANISM: Homo sapiens

<400> SEQUENCE: 9

Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140
```

-continued

```
Lys Ile Gly Lys Glu Phe Lys Arg Ile Val Gln Arg Ile Asp Asp Phe
145                 150                 155                 160

Leu Arg Asn Leu Val Pro Arg Thr Glu Ser
                165                 170
```